United States Patent
Mao et al.

(10) Patent No.: US 12,310,682 B2
(45) Date of Patent: May 27, 2025

(54) SYSTEMS AND METHODS FOR MOUNTING ROBOTIC COMPONENTS ON A LOAD CELL

(71) Applicant: Auris Health, Inc., Redwood City, CA (US)

(72) Inventors: Ying Mao, San Mateo, CA (US); Aren Calder Hill, Mountain View, CA (US); Alex C. Spies, Redwood City, CA (US); Nicholas J. Eyre, Redwood City, CA (US); Yanan Huang, Sunnyvale, CA (US)

(73) Assignee: Auris Health, Inc., Santa Clara, CA (US)

( * ) Notice: Subject to any disclaimer, the term of this patent is extended or adjusted under 35 U.S.C. 154(b) by 931 days.

(21) Appl. No.: 17/167,933

(22) Filed: Feb. 4, 2021

(65) Prior Publication Data
US 2021/0298847 A1    Sep. 30, 2021

Related U.S. Application Data

(60) Provisional application No. 63/003,034, filed on Mar. 31, 2020.

(51) Int. Cl.
*A61B 34/30* (2016.01)

(52) U.S. Cl.
CPC ........ *A61B 34/30* (2016.02); *A61B 2034/305* (2016.02); *A61B 2562/0252* (2013.01)

(58) Field of Classification Search
None
See application file for complete search history.

(56) References Cited

U.S. PATENT DOCUMENTS

| | | | |
|---|---|---|---|
| 5,737,500 A | 4/1998 | Seraji et al. | |
| 6,063,095 A * | 5/2000 | Wang | A61B 34/37 606/139 |
| 6,459,926 B1 | 10/2002 | Nowlin et al. | |
| 8,004,229 B2 | 8/2011 | Nowlin et al. | |
| 8,749,189 B2 | 6/2014 | Nowlin et al. | |

(Continued)

FOREIGN PATENT DOCUMENTS

| | | |
|---|---|---|
| JP | 2017071018 A | 4/2017 |
| WO | WO-2017013450 A1 | 1/2017 |

OTHER PUBLICATIONS

Choi, et al., "A Force/Moment Direction Sensor and Its Application in Intuitive Robot Teaching Task," ICASE: The Institute of Control, Automation and Systems Engineers, Korea, Dec. 2001, vol. 3, No. 4, pp. 236-241.

(Continued)

*Primary Examiner* — Vicky A Johnson
(74) *Attorney, Agent, or Firm* — Frost Brown Todd LLP

(57) ABSTRACT

Certain aspects relate to a robotic surgery system, including a robotic arm with a base, a proximal portion and a distal portion. A tool driver is detachably coupled to a medical instrument and the tool driver is coupled with the distal portion of the robotic arm. A load cell is positioned between the proximal portion and the distal portion such that the load cell supports the distal portion and the tool driver. The load cell is configured to detect forces that interact with the distal portion or the tool driver to enhance user control of the robotic arm and/or the safe operation of the robotic arm.

20 Claims, 25 Drawing Sheets

(56) References Cited

U.S. PATENT DOCUMENTS

| | | |
|---|---|---|
| 8,786,241 B2 | 7/2014 | Nowlin et al. |
| 8,823,308 B2 | 9/2014 | Nowlin et al. |
| 9,687,310 B2 | 6/2017 | Nowlin et al. |
| 9,763,741 B2 | 9/2017 | Alvarez et al. |
| 10,123,844 B2 | 11/2018 | Nowlin et al. |
| 10,194,998 B2 | 2/2019 | Nowlin et al. |
| 10,512,514 B2 | 12/2019 | Nowlin et al. |
| 2009/0248038 A1 | 10/2009 | Blumenkranz et al. |
| 2012/0029529 A1 | 2/2012 | Jun et al. |
| 2014/0276594 A1 | 9/2014 | Tanner et al. |
| 2018/0071035 A1 | 3/2018 | Marshall et al. |
| 2018/0116741 A1* | 5/2018 | Garcia Kilroy ....... G01L 3/1428 |
| 2018/0215054 A1 | 8/2018 | Brudniok |
| 2019/0105785 A1 | 4/2019 | Meyer et al. |

OTHER PUBLICATIONS

Whitney, "Force Feedback Control of Manipulator Fine Motions," Journal of Dynamic Systems, Measurement and Control, Jun. 1977, pp. 91-97.
International Search Report of International Application No. PCT/IB2021/050919, dated May 7, 2021, 4 pages.
International Preliminary Report on Patentability of International Application No. PCT/IB2021/050919, dated Oct. 13, 2022, 7 pages.
Written Opinion of the International Searching Authority of International Application No. PCT/IB2021/050919, dated May 7, 2021, 5 pages.
European Extended Search Report; Application No. 21782280.8; Jan. 18, 2024; 11 pages.

* cited by examiner

SYSTEMS AND METHODS FOR MOUNTING ROBOTIC COMPONENTS ON A LOAD CELL

CROSS REFERENCE

This application claims the benefit of priority to U.S. Provisional Application No. 63/003,034 the entire contents of which are hereby incorporated by reference.

TECHNICAL FIELD

The systems and methods disclosed herein are directed to surgical robotic systems and the novel integration of a load cell in a robotic arm for a surgical system.

BACKGROUND

Surgical robotic systems can include a robotic arm for supporting and manipulating a medical instrument. The medical instrument can be mounted on an end effector of the robotic arm. The robotic arm can include a series of articulable joints connected by linkages. In certain implementations the robotic arm can be manipulated by a surgeon via teleoperation to conduct a surgical procedure using the robotic arm and medical instrument.

SUMMARY

One aspect of the present disclosure is the integration of one or more load cells within a surgical robotic system. The surgical robotic system can include a robotic arm. The arm can comprise a plurality of independently articulable joints and linkages for controlling the position of an end effector. The end effector can support a medical instrument for conducting any of various surgical procedures. The position of the linkages in the robotic arm and/or the medical instrument can be controlled by a physician via teleoperation. In addition to teleoperation of the surgical robotic system it can be desirable to manipulate the robotic arm in response to other exterior stimuli. In one example, it can be beneficial to detect and/or measure forces applied on portions on the robotic system such as the medical instrument or any of the linkages or joints of the robotic arm. It can also be desirable to manipulate the robotic arm in response to direct user inputs (e.g. manual manipulation of the robotic arm in a robotically assisted movement mode).

Thus according to another aspect of the present disclosure it has been found that it can be beneficial to incorporate a load cell within the robotic arm. The load cell in certain cases can be or include a plurality of force sensors situated to detect forces and/or moments on a distal portion of the robotic arm. By incorporating the load cell, the robotic arm can directly sense and measure interaction forces such as from a user. The interactive forces can be applied by a clinician engaging with the robot or the robot engaging with an object within the environment around the robotic arm. The incorporation of the load cell into the robotic arm can also be useful for safety sensing. The robotic arm can measure forces or moments that are contacting with a patient, clinician or other objects. If the forces are detectable, the robot can be programmed to limit the forces applied to the exterior objects and prevent further harm or damage to the patient, object or the robotic arm itself.

One aspect of the present disclosure is a robotic surgery system that includes a robotic arm. The robotic arm can include a base having a proximal portion and a distal portion. The tool driver can detachably couple to a medical instrument. The tool driver can be coupled with the distal portion of the robotic arm. A load cell can be positioned between the proximal portion and the distal portion such that the load cell supports the distal portion and the tool driver. The load cell is configured to detect forces that interact with the distal portion of the tool driver.

According to another aspect, a structural break between the proximal portion and the distal portion is bridged by the load cell.

According to another aspect, the load cell entirely supports the distal portion of the robotic arm and the tool driver.

According to another aspect, the load cell is positioned adjacent a wrist joint of the robotic arm.

According to another aspect, the load cell is positioned between a first joint and a second joint of the robotic arm.

According to another aspect, the first joint is a wrist roll joint and the second joint is a wrist pitch joint.

According to another aspect, the load cell is positioned adjacent the base of the robotic arm.

According to another aspect, the load cell is a multi-axis load cell.

According to another aspect, the load cell is a three-axis load cell.

According to another aspect, the load cell is a six-axis load cell.

According to another aspect, the load cell includes a plurality of load cells. The plurality of load cells are configured to together detect one or more forces and/or moments on the distal portion of the robotic arm.

According to another aspect, the plurality of load cells includes at least three load cells.

According to another aspect, the three load cells are arranged in a tripod configuration.

According to another aspect, the load cells of the plurality of load cells are single-axis load cells.

According to another aspect, the first load cell and the robotic arm further include a second load cell position between the base and the first load cell. The second load cell supports the first load cell and the distal portion includes the tool driver. The second load cell can detect forces that interact with any portion of the robotic arm or tool driver distal to the second load cell.

According to another aspect, the load cell includes a first shell member and a second shell member. The first shell member is coupled with the distal portion of the robotic arm. The second shell member is coupled with the proximal portion of the robotic arm.

According to another aspect, the load cell is configured to detect interaction forces between a patient and/or cannula and the tool driver or another portion of the distal portion.

According to another aspect, the robotic surgery system includes a robotic arm having a base of a proximal portion and the distal portion. A tool driver detachably couples to a medical instrument. The tool driver is coupled with the distal portion of the robotic arm. A load cell is positioned between the proximal portion and the distal portion. The load cell forms a structural break between the proximal portion and the distal portion such that the load cell entirely supports the distal portion including the tool driver.

According to another aspect, the load cell is positioned adjacent a wrist joint of the robotic arm.

According to another aspect, the load cell is positioned between a first joint and a second joint of the robotic arm.

According to another aspect, the first joint is a wrist roll joint and the second joint is a wrist pitch joint.

According to another aspect, the load cell is positioned adjacent the base of the robotic arm.

According to another aspect, the load cell is a multi-axis load cell.

According to another aspect, the load cell is a three-axis load cell, a six-axis load cell, and a plurality of force sensors.

According to another aspect, the load cell is configured to detect interaction forces between a patient and/or cannula and the tool driver or medical instrument.

According to another aspect, the robotic surgery system includes a robotic arm having a tool driver capable of coupling with the detachable instrument. A load cell for detecting a force that interacts with the robotic arm enables manual manipulation of the robotic arm. The tool driver is mounted on the load cell.

According to another aspect a robotic surgery system includes a robotic arm having a base, a proximal portion and a distal portion. The tool driver detachably couples to a medical instrument on the distal portion of the robotic arm. The robotic arm includes a multi-axis load cell positioned between the proximal portion and the distal portion. The multi-axis load cell bridges a structural break between the proximal portion and the distal portion.

According to another aspect, the multi-axis load cell includes a plurality of force sensors configured to detect loads on the distal portion or tool driver or other robotic arm.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
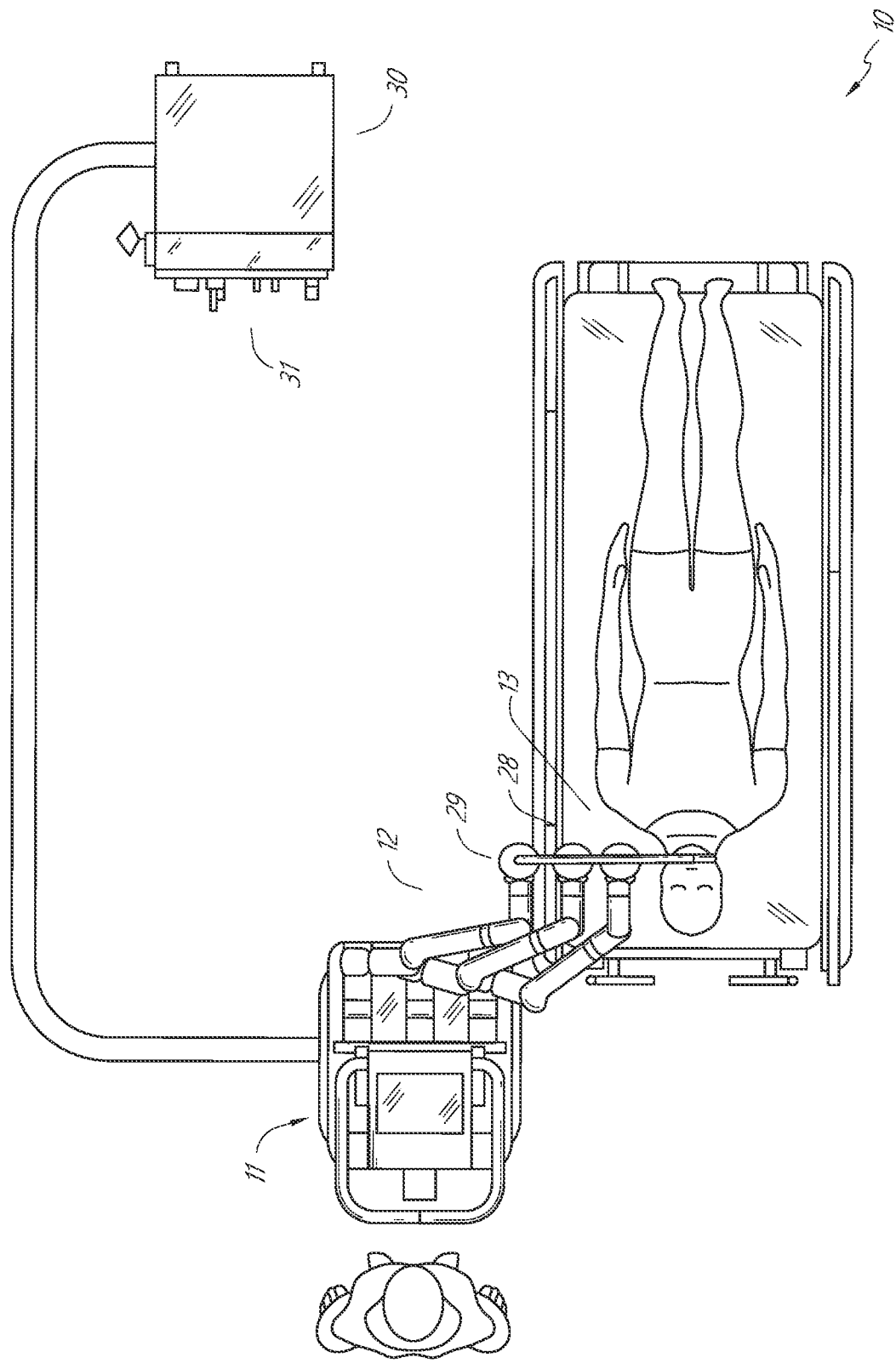
FIG. 1 illustrates an embodiment of a cart-based robotic system arranged for diagnostic and/or therapeutic bronchoscopy.
Figure 2:
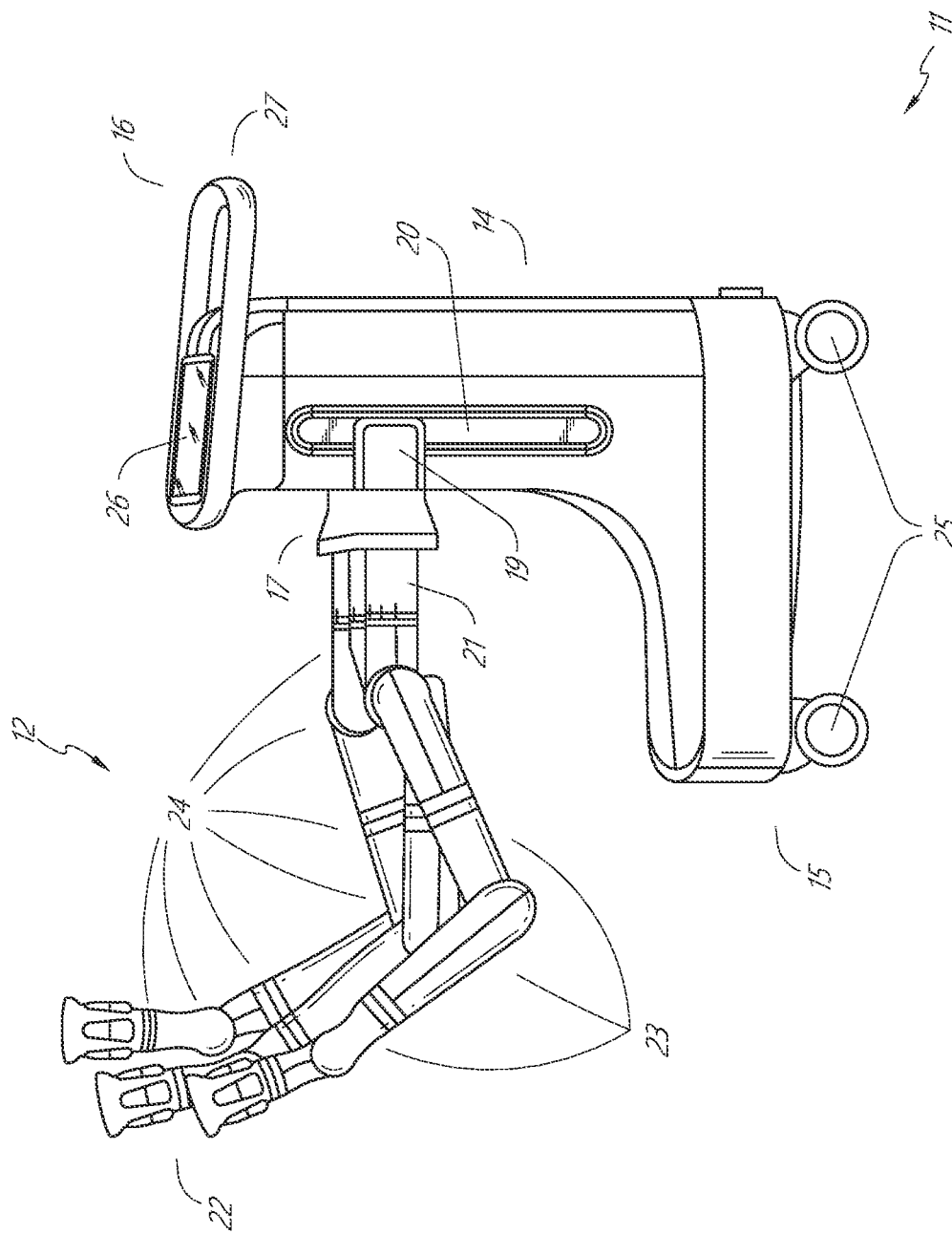
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to respect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
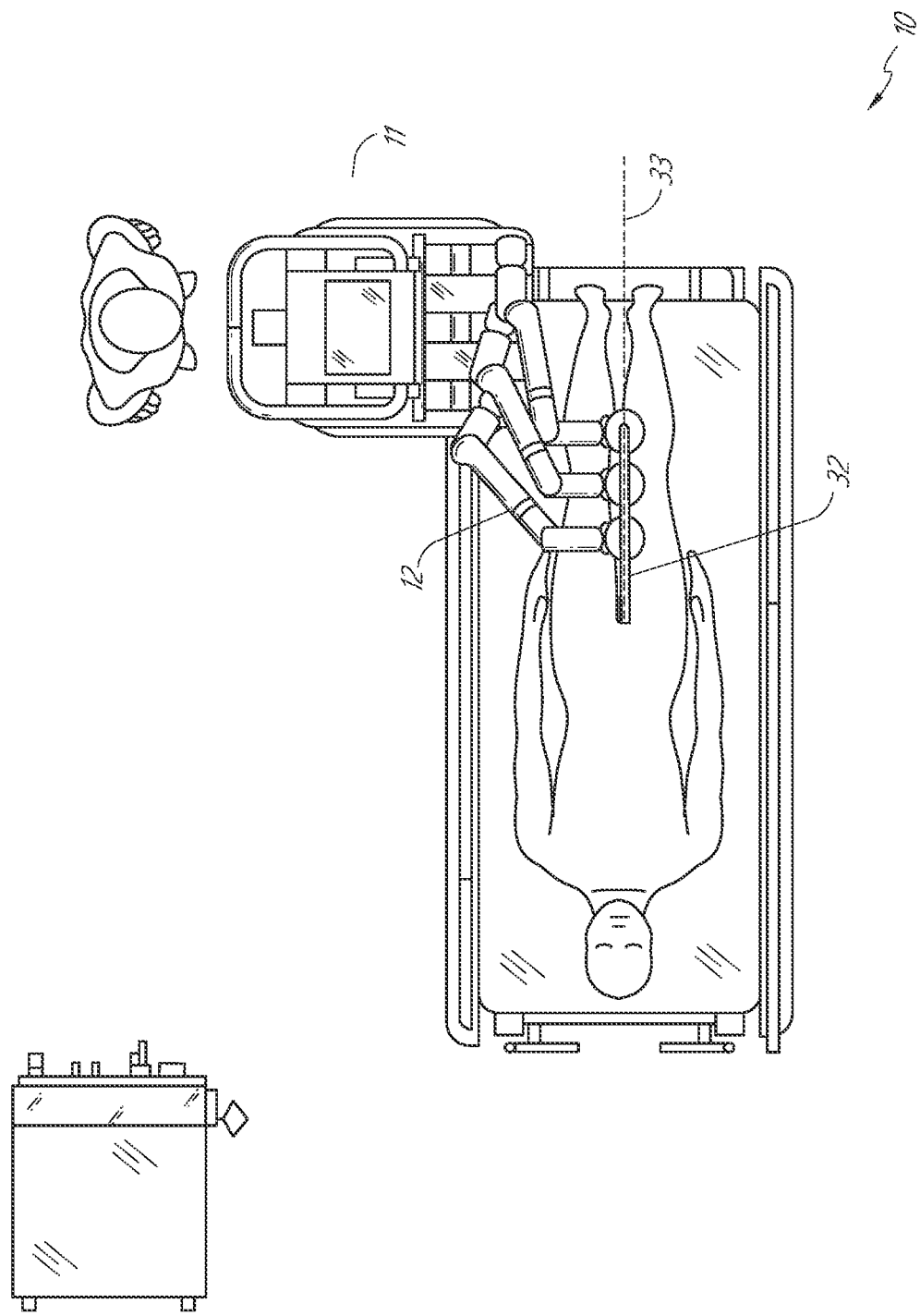
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
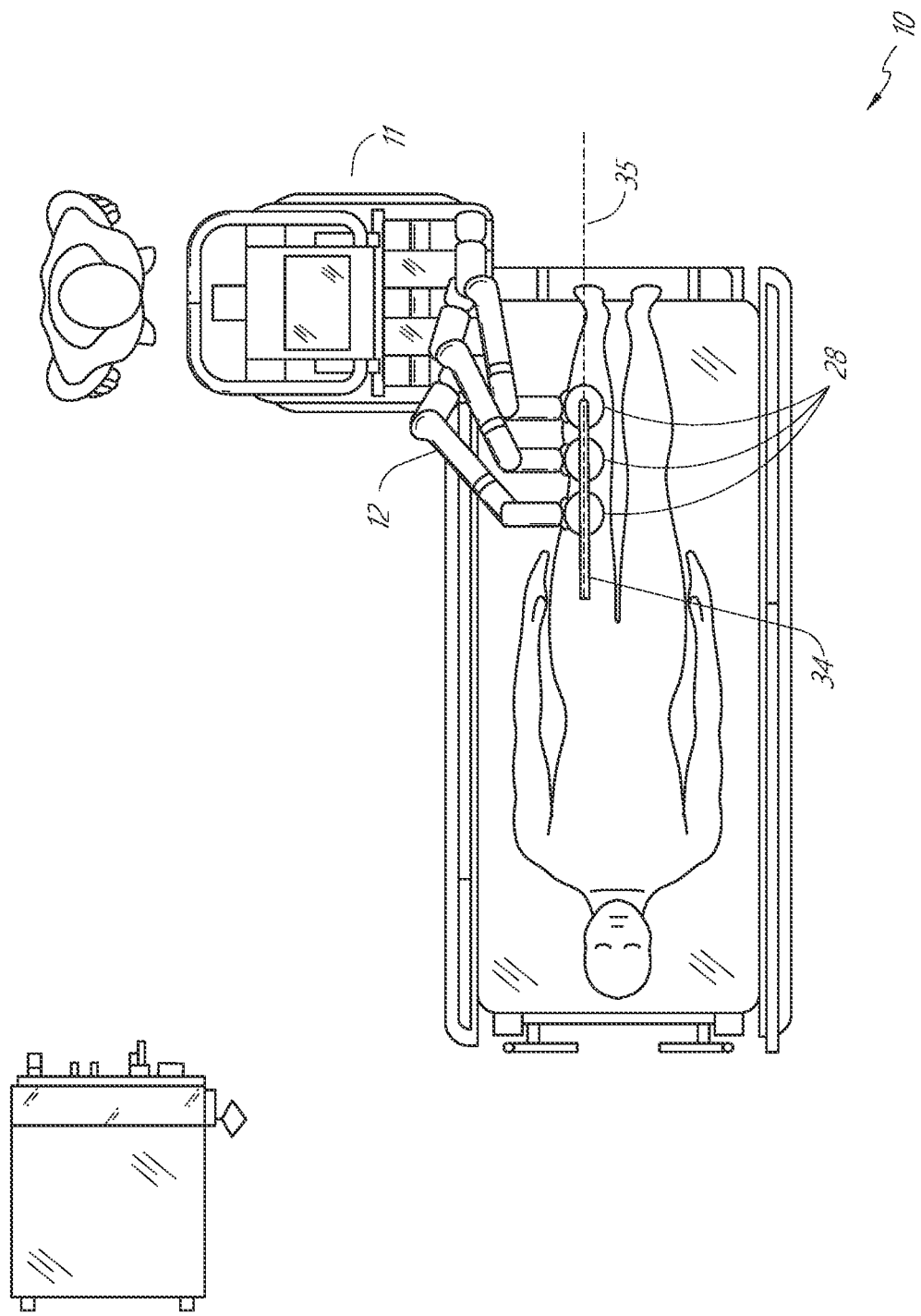
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
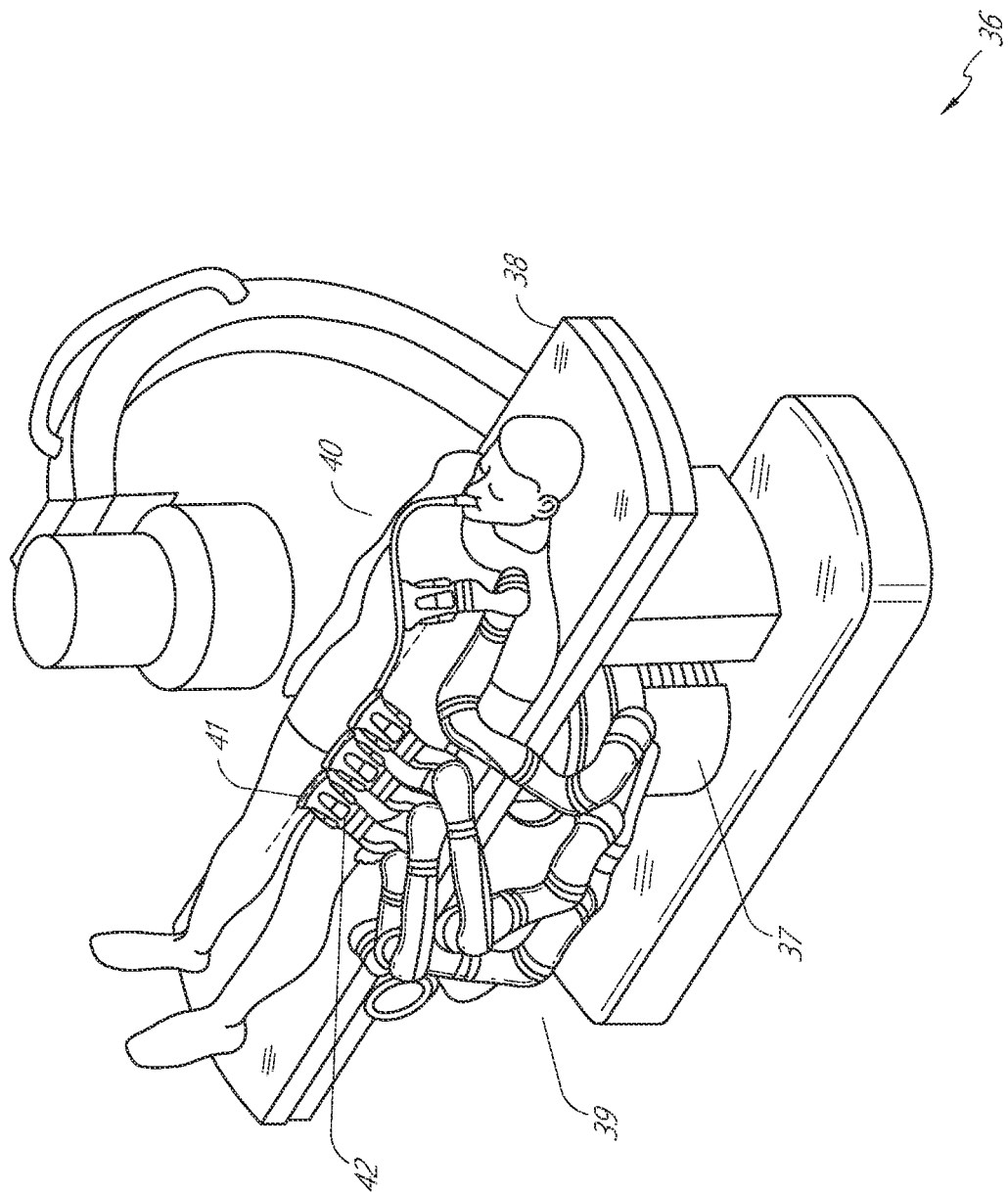
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
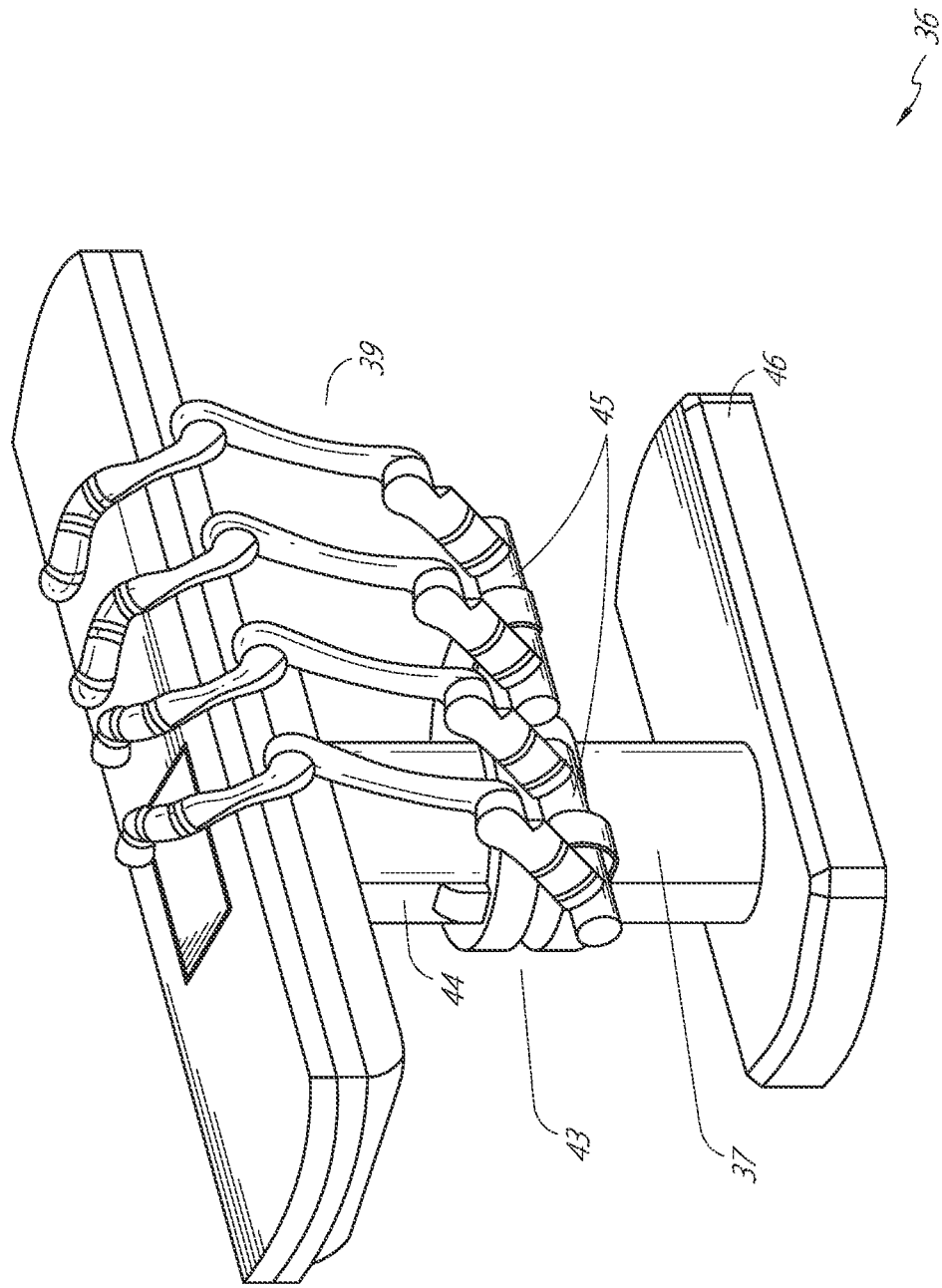
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
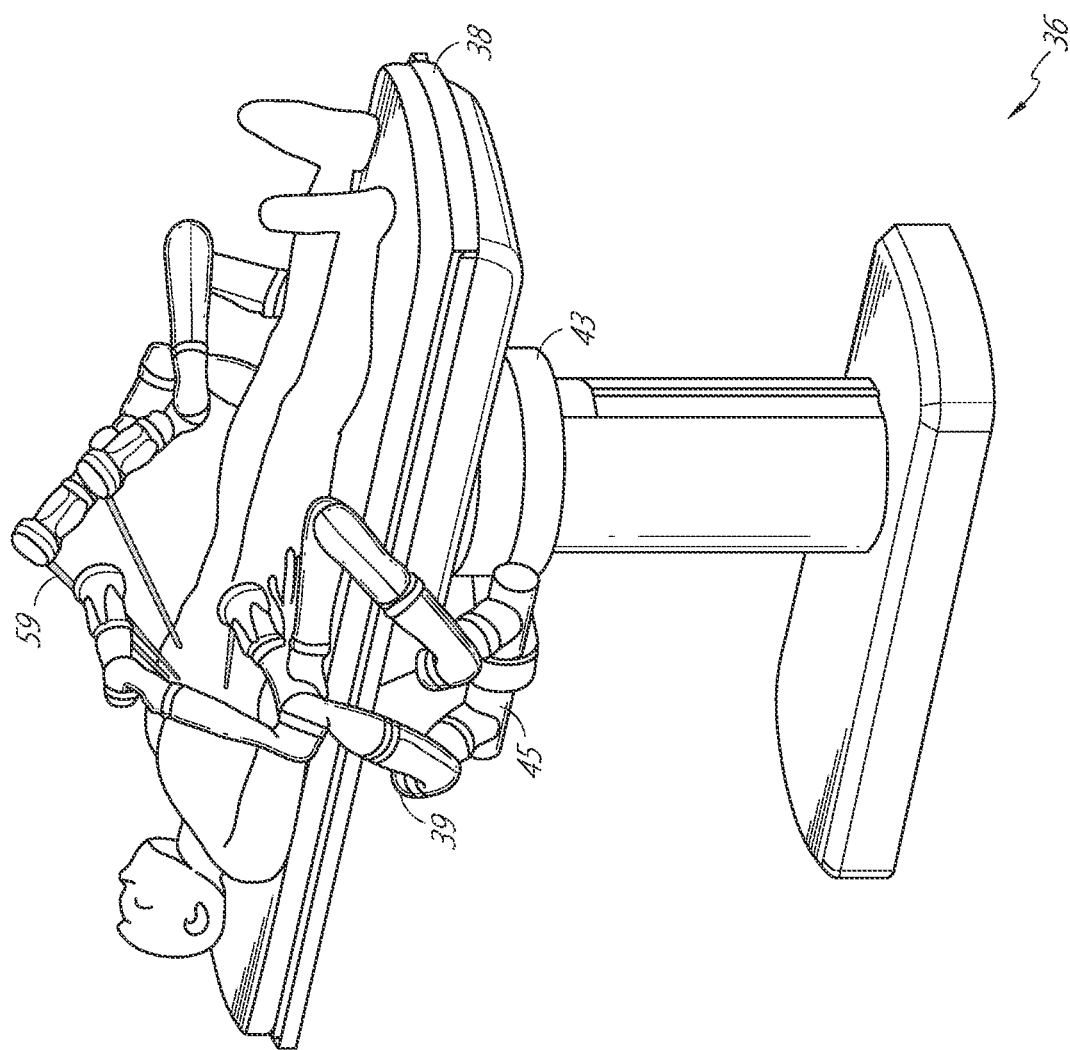
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intraoperative information, such as real-time imaging, navigation, and tracking information. In some embodiments, the tower may also contain holders for gas tanks to be used for insufflation.

Figure 7:
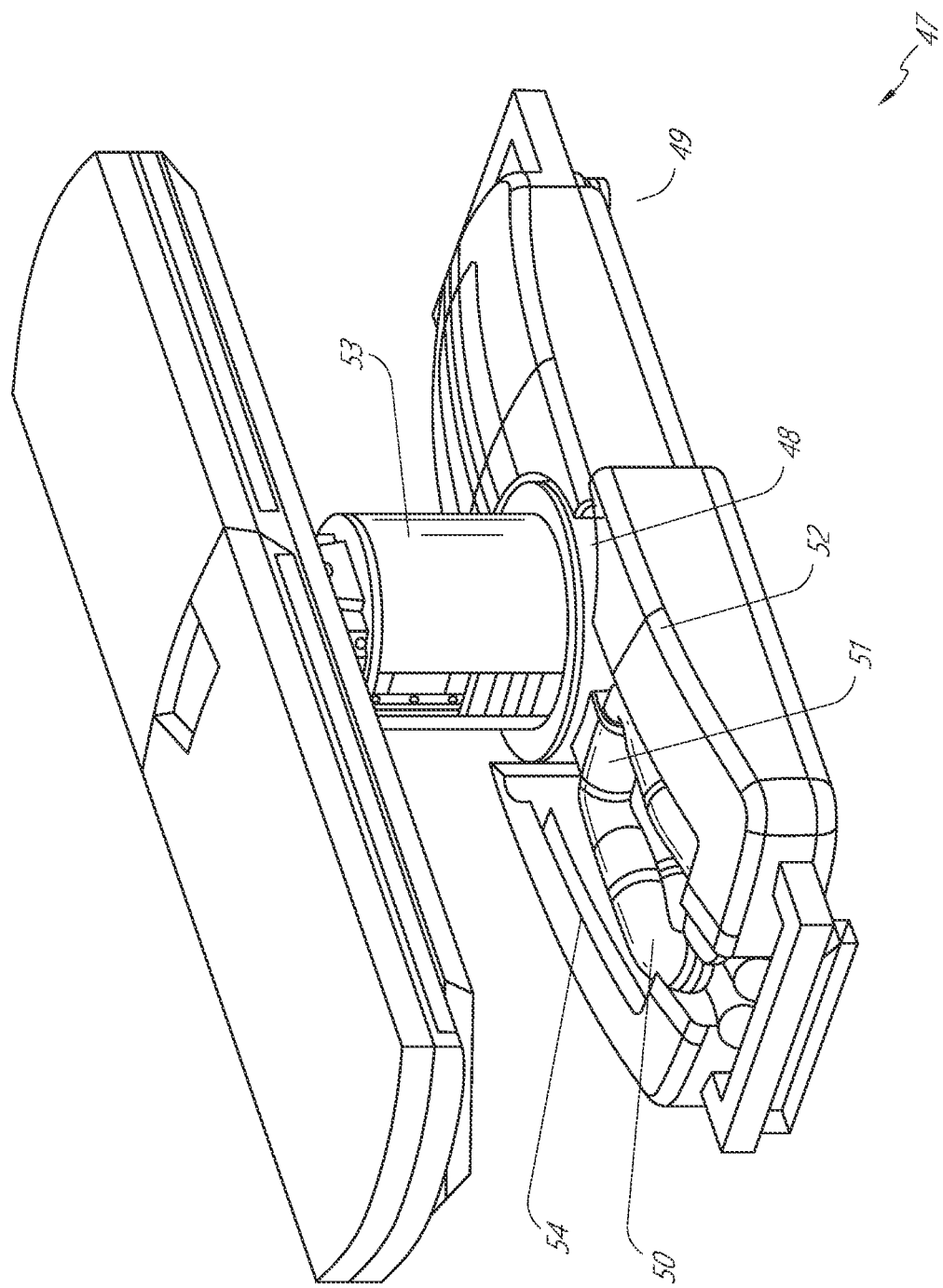
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
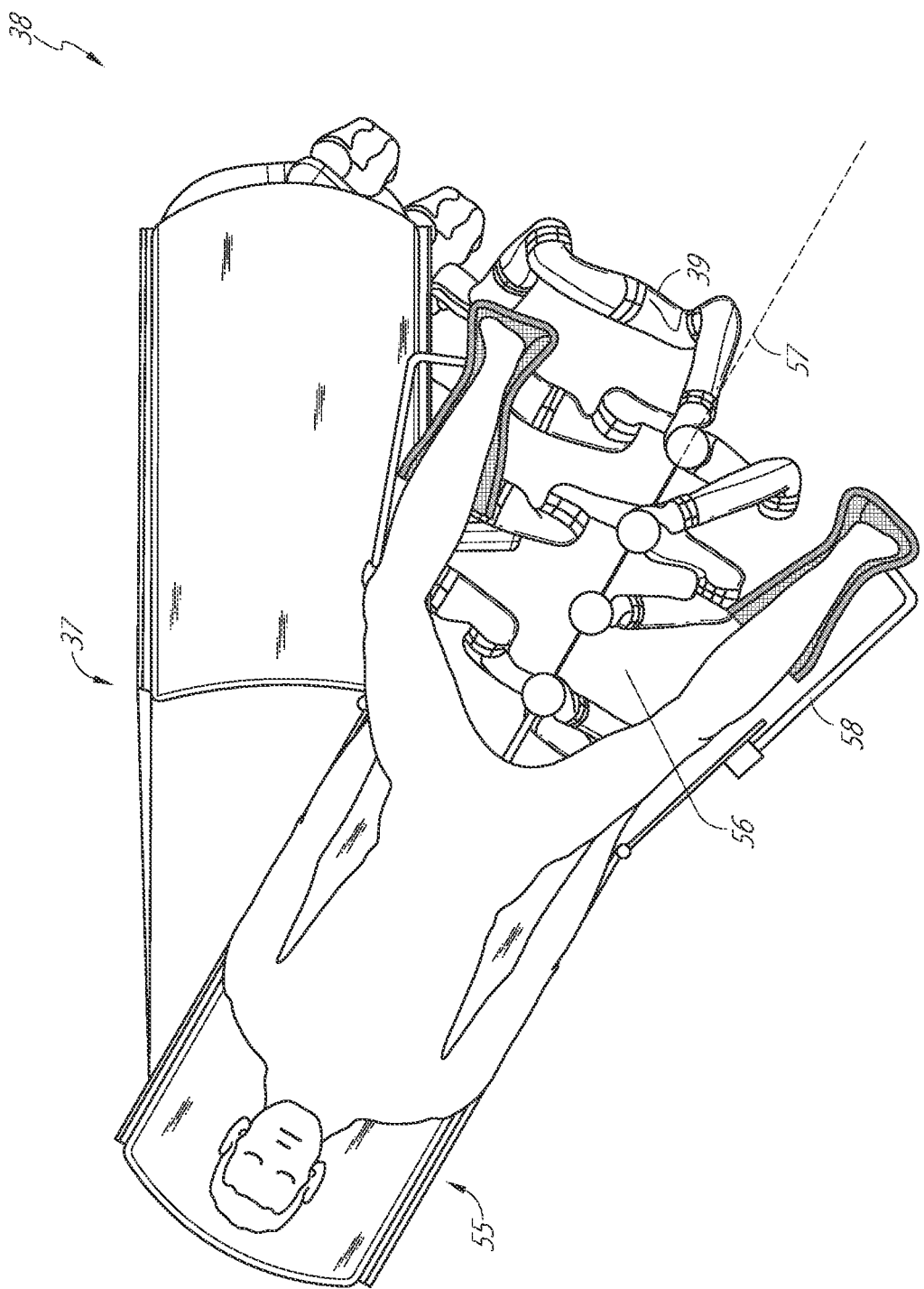
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown)

below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
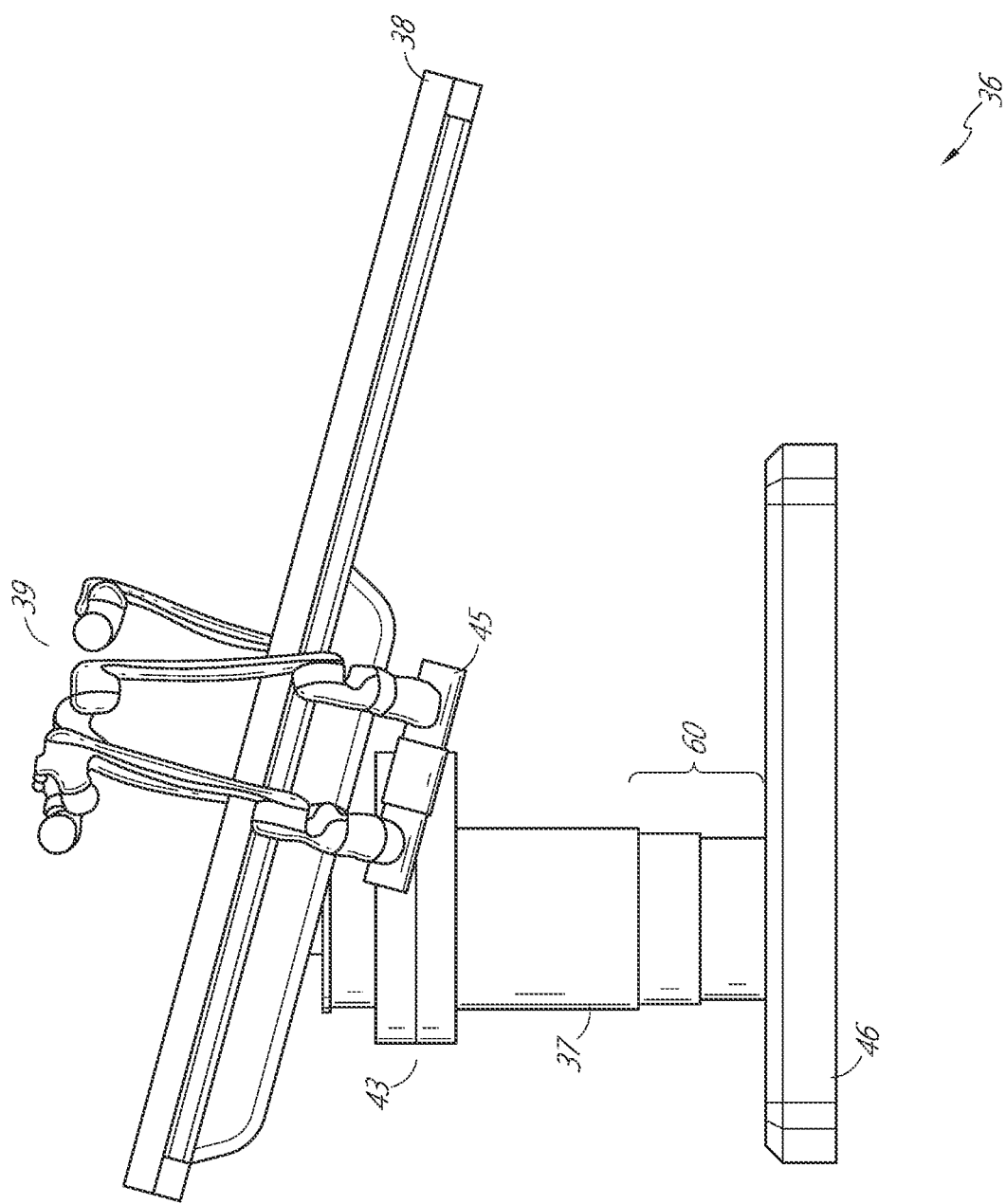
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
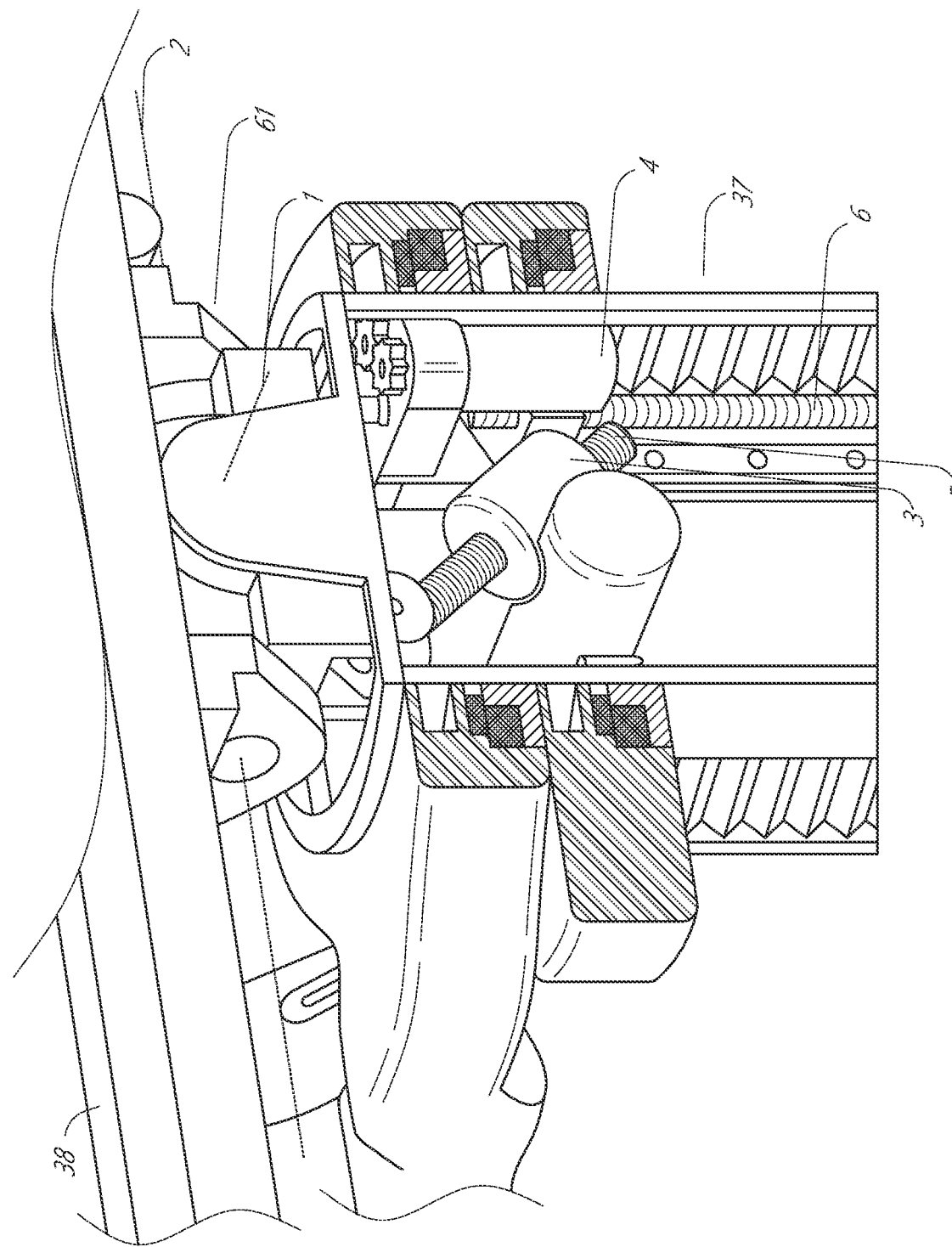
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
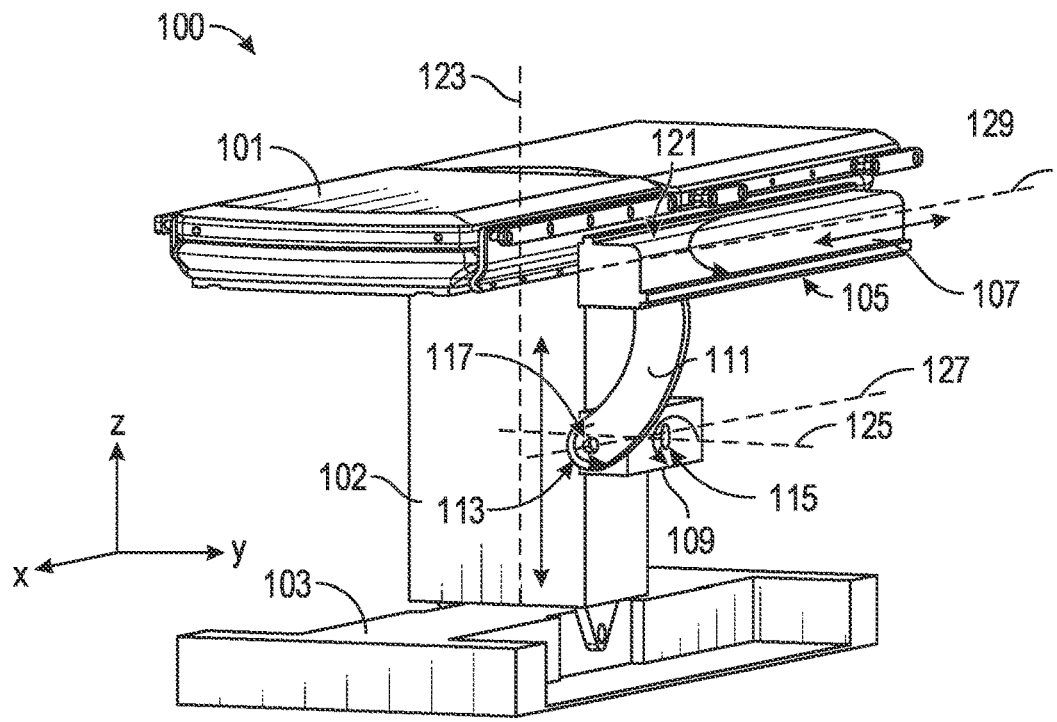
FIG. 12 illustrates an alternative embodiment of a table-based robotic system.
Figure 13:
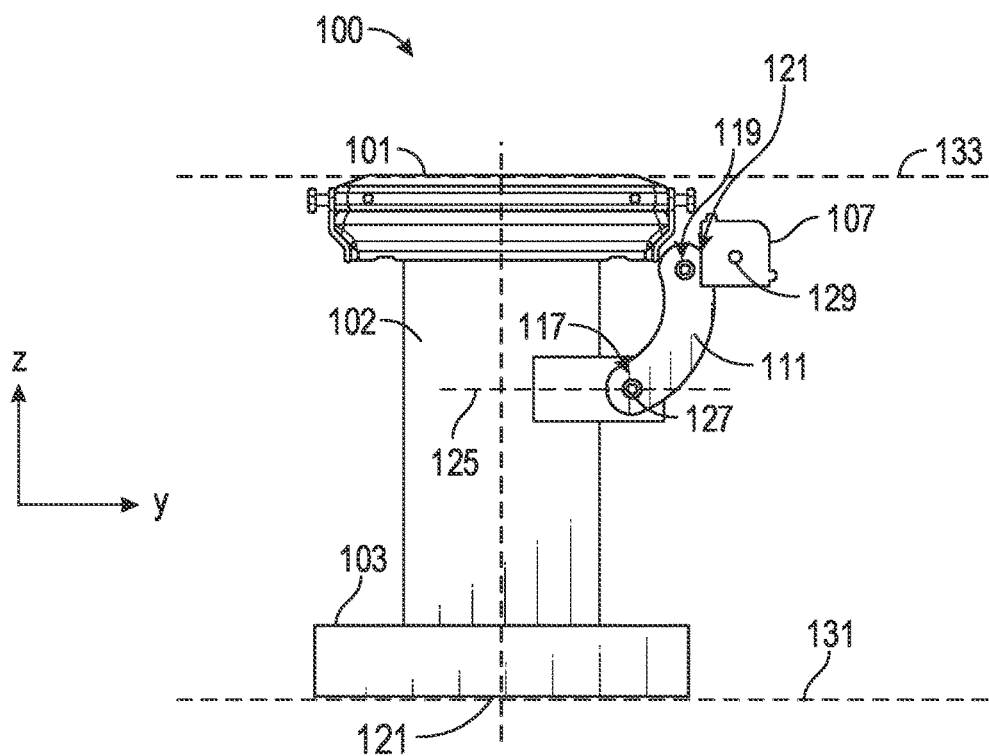
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
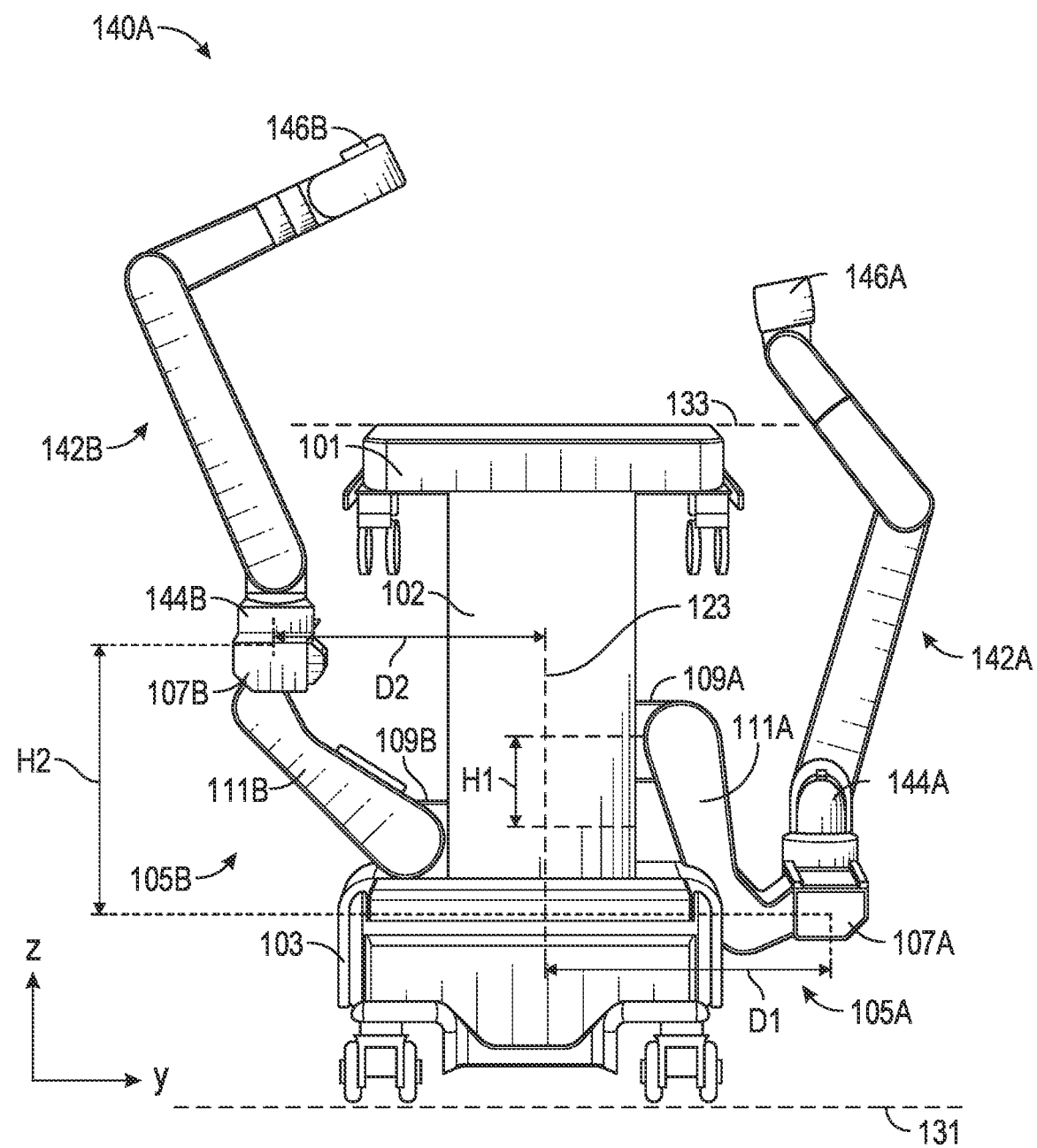
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
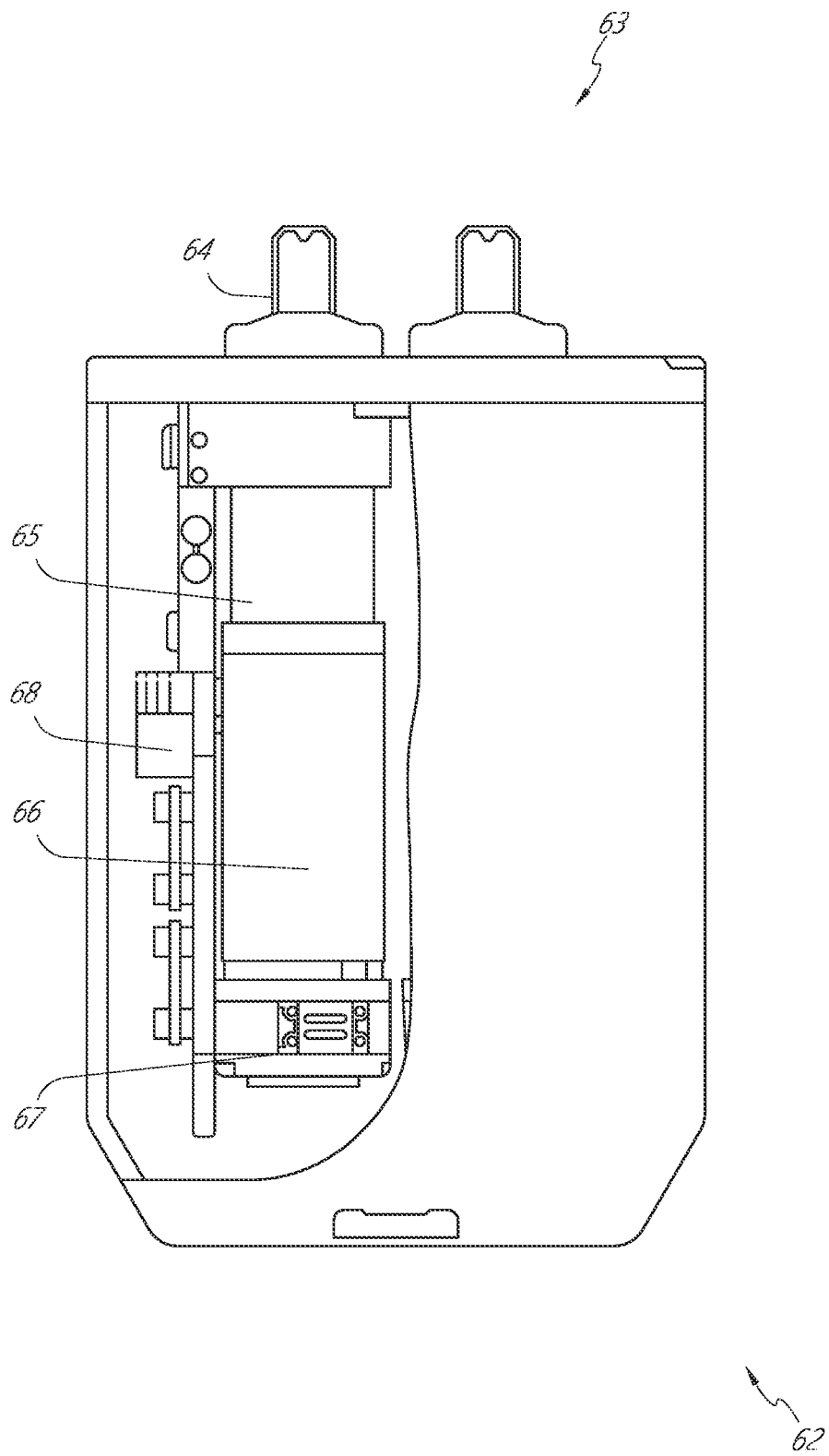
FIG. 15 illustrates an exemplary instrument driver.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
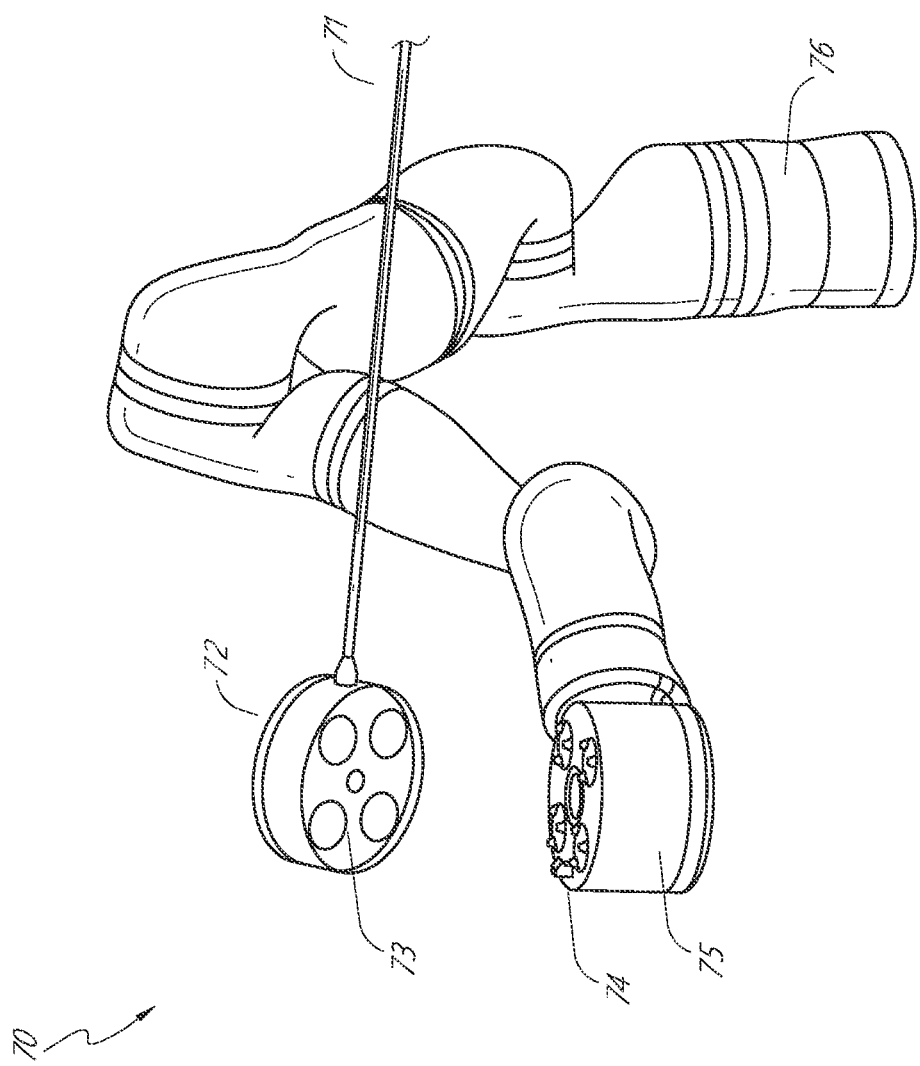
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
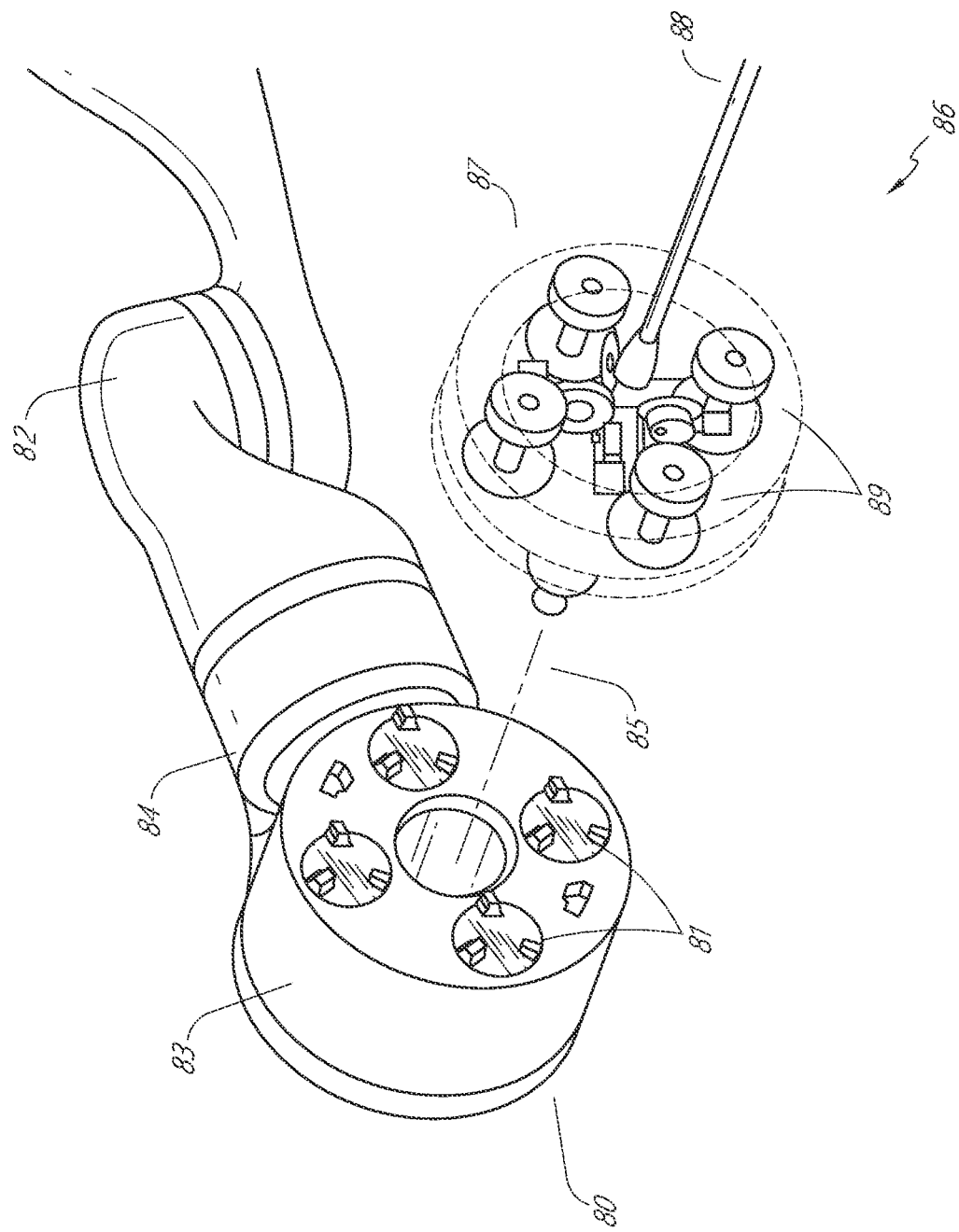
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
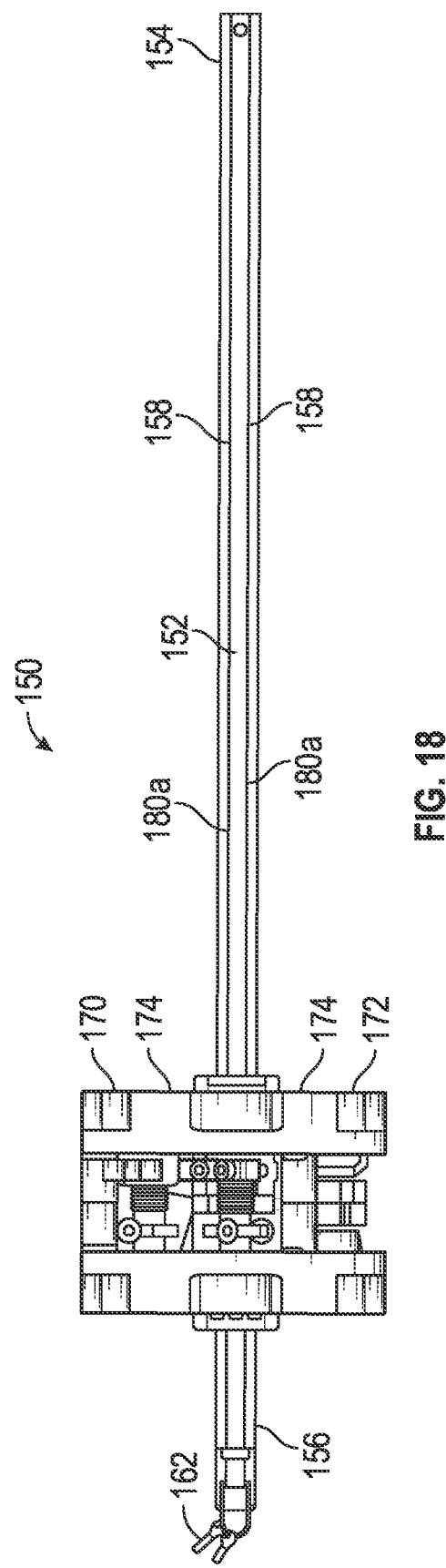
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
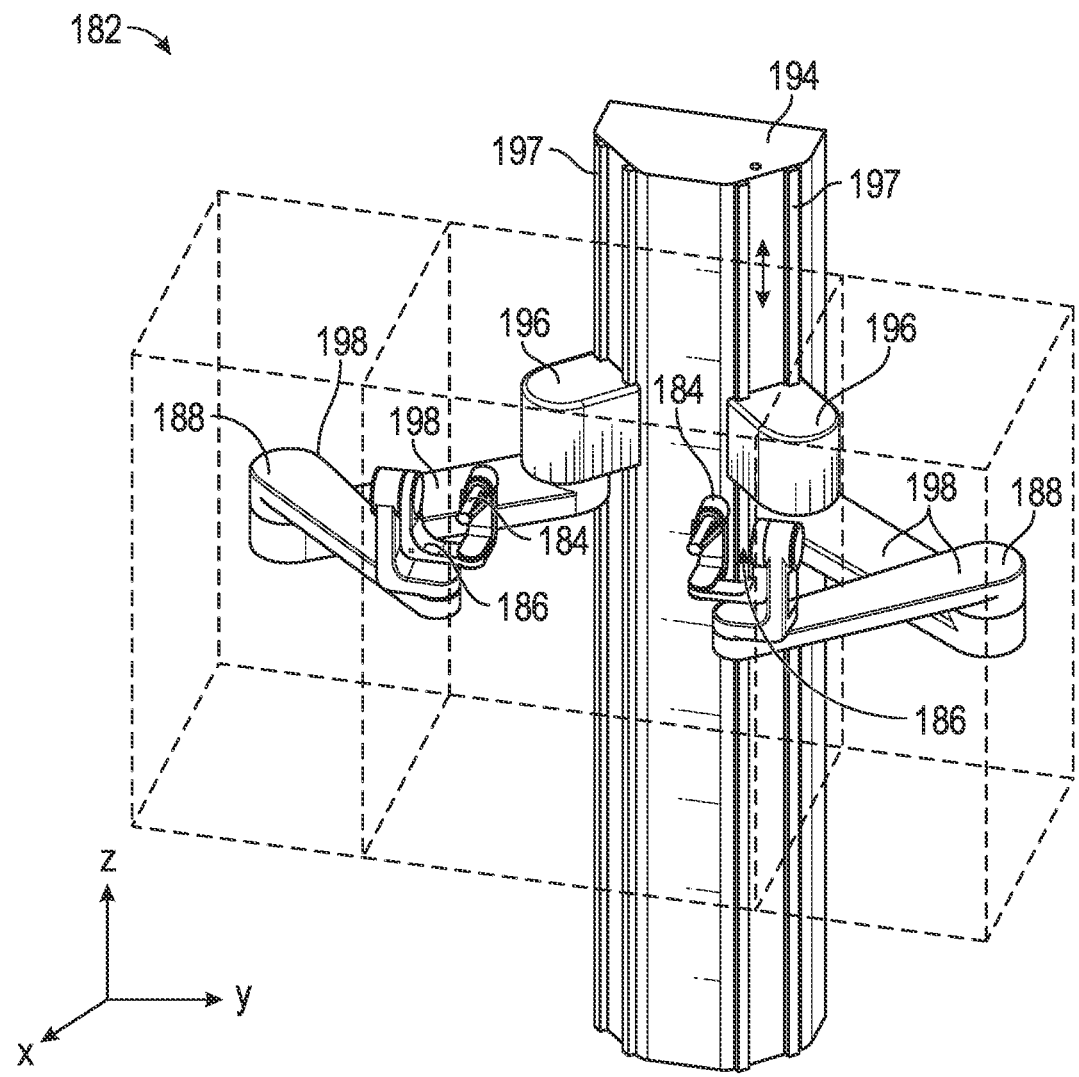
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
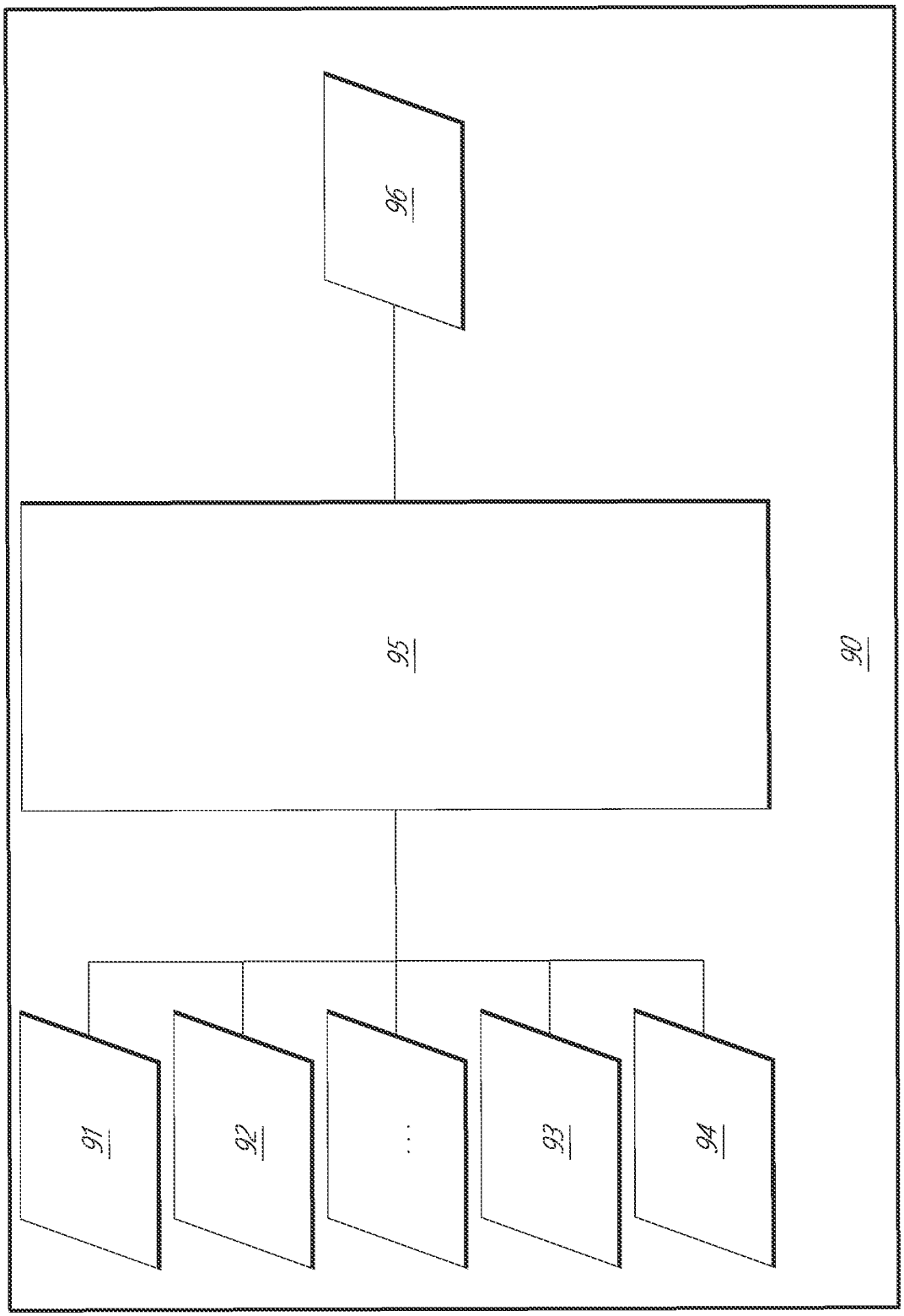
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Introduction to Robotic Arms and Load Cells

Surgical robotic systems according to the present disclosure include a robotic arm with one or more integrated load cells therein. The one or more load cells can measure forces acting on the robotic arm. Accordingly, the load cells can be used to improve user control of the robotic arm and/or safe operation of the robotic arm during medical procedures. By incorporating one or more load cells, the robotic arm can directly sense and measure interaction forces from a user. In other words, by incorporating a load cell into the robotic arm, the robotic arm can then detect interactive forces that are applied on the robotic arm (e.g., via a clinician or clinician assistant). Advantageously, in some embodiments, the one or more load cells can sense both forces and torques/moments. The incorporation of a load cell into a robotic arm can also be used for safety sensing—to detect if the portion of the robot arm distal of the load cell has contacted a patient, a member of bedside staff, or an object near the bedside. If such contact is detected, the robot can stop to prevent further harm after contacting something.

In some embodiments, a load cell is positioned along a length of a robotic arm in a location of a structural break. Accordingly, portions of the robotic arm that are distal to the load cell can be mounted and supported by the load cell, and interactions with these distal portions can be detected by the load cell. In some embodiments, this novel configuration of the load cell allows for a robotic to directly measure interaction forces with a user, as well as semi-direct measurement of contact forces that the distal end of the robotic arm might apply on a patient or on objects that collide with it. In addition, in some embodiments, this novel configuration allows for direct measurement of cannula loads being applied by the robot to the body wall of a patient. Details of the unique configuration of the robotic arm including one or more load cells, as well as the types of load cells, are provided below.

Figure 21A:
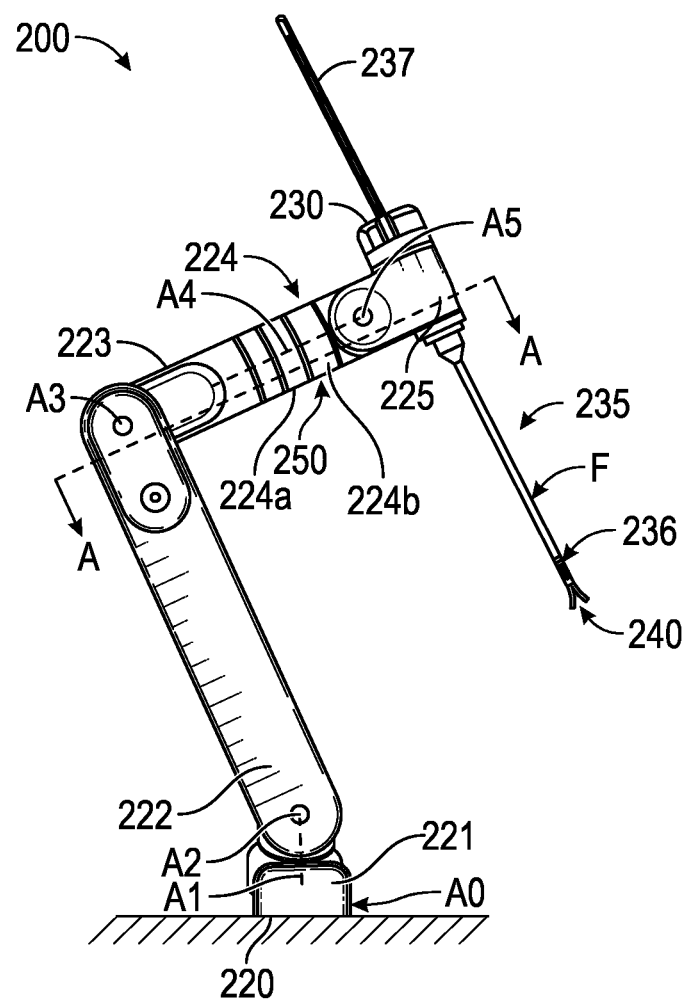
FIG. 21A shows an example of a robotic arm including a load cell.
Figure 21B:
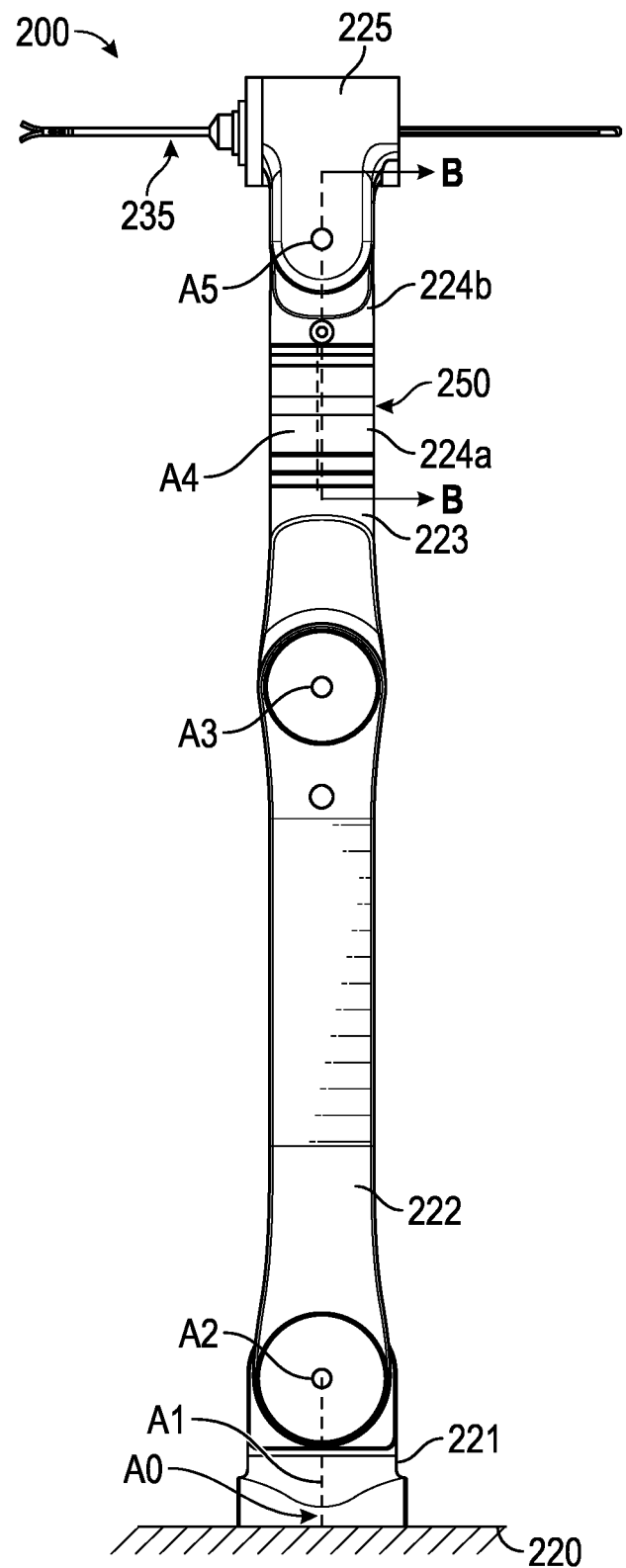
FIG. 21B shows a front view of the robotic arm in FIG. 21A.

FIG. 21A shows an example of a robotic arm 200, which can be a component of a robotic surgical system. The robotic arm 200 can include a series of linkages connected by independently articulable joints. The independently articulable joints can include joints A0, A1, A2, A3, A4 and/or A5. The joints A0-A5 can variously include rotation and/or translation joints. The robotic arm 200 can have six or more degrees of freedom.

The series of linkages can include a support rail 220, a first link 221, a second link 222, a third link 223, a fourth link 224, and/or a fifth link 225. The support rail 220 can be coupled with the first link 221 at the base joint A0. The first link 221 can be translatable along the support rail 220. The first link 221 can be coupled with the second link 222 by the first and second joints A1, A2. The second link 222 can be rotatable about two axes with respect to the first link 221. The second link 222 can be coupled with the third link 223 by the third joint A3. The third joint A3 can be an elbow joint. The third link 223 can be rotatable about one axis with respect to the second link 222. The third link 223 can be coupled with the fourth link 224 by the fourth joint A3. The fourth link 224 can be rotatable about one axis with respect to the third link 223 (e.g., along a shaft aligned along a longitudinal axis of both the third and fourth link 223, 224). The fourth link 224 can be coupled with the fifth link 225 by the fifth joint A5. The fifth link 225 can be rotatable about one axis with respect to the fourth link 224. The fourth and fifth joints A4, A5 can form a wrist joint of the robotic arm 200. The fourth joint A4 can be a roll joint and the fifth joint A5 can be a pitch joint.

The robotic arm 200 can include a tool driver 230. The tool driver 230 can be located on a distal end of the robotic arm 200 (e.g., on the fifth link 225). The tool driver 230 can be removably coupled with a medical instrument 235. The medical instrument 235 can include an elongate shaft. The elongate shaft can extend from a first end 236 to a second end 237. The first end 236 can include an end effector 240. The end effector 240 can be any of various medical instruments such as but not limited to grippers, lances, probes, endoscopes, shears or other surgical tools.

The position of the medical instrument 235 can be controlled by the tool driver 230 and the articulable joints of the robotic arm 200. The robotic arm 200 can be positionable in response to user inputs via teleoperation. A physician or other user can also manually manipulate the robotic arm 200. In certain, implementations, the user can back drive the articulable joints, for example, to dock the tool driver 230 with a cannula or fold the robotic arm 200 for storage. In low inertia systems, back driving the articulable joints can be relatively easy. However, in high inertia systems, back driving the articulable joints can be difficult. Accordingly, the load cell 255 can be used to detect manipulation forces. In certain operation modes, the robotic arm 200 can be programed to move in response to such external manipulation forces.

In some embodiments, the robotic arm 200 can include a structural break 250. The structural break 250 can physically separate a distal portion of the robotic arm from a proximal portion of the robotic arm. The structural break 250 can physically separate a distal portion of any of the linkages from a proximal portion of the linkage. The structural break can entirely sever mechanical connection between the proximal portion and the distal portion. For example, the linkage can include one or more inner structural members and/or one or more outer shell or exterior portions. The structural break 250 can extend through both the inner structural members and the outer shell portions.

As illustrated, the structural break 250 is positioned in the fourth link 224. In other implementations, the structural break 250 can be located within any of the linkages. The fourth link 224 can include a proximal portion 224a and a distal portion 224b. The structural break 250 can separate the proximal portion 224a and the distal portion 224b.

Advantageously, the structural break 250 can be bridged by a load cell 255. The load cell 255 can include a first end 255a and a second end 255b. The load cell 255 can include an outer shell formed of first and second shell members. The first shell member can include the first end 255a. The second shell member can include the second end 255b. The first shell member can be rigidly coupled with the proximal portion 224a. The second shell member can be rigidly coupled with the distal portion 224b.

Figure 22A:
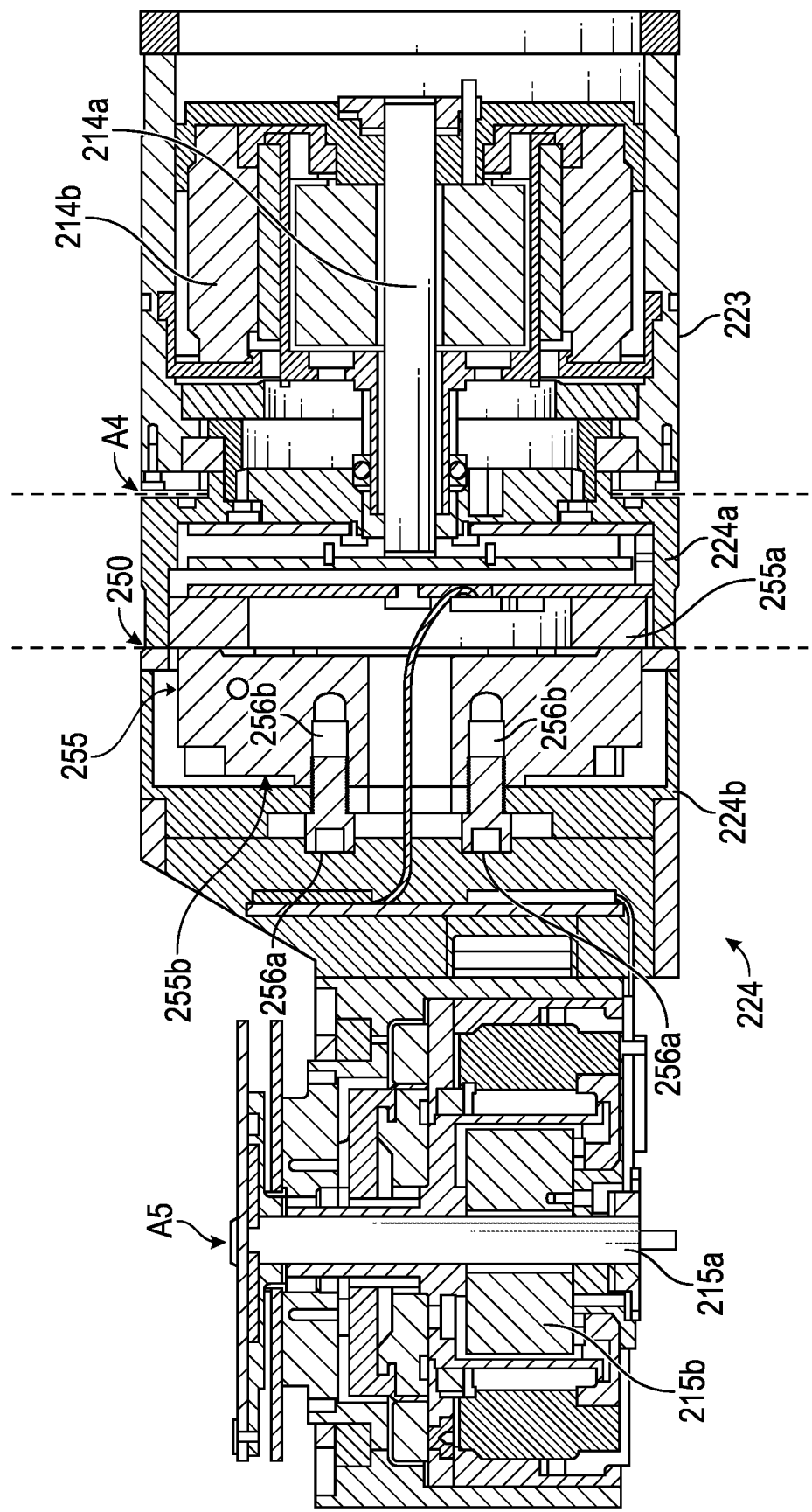
FIG. 22A shows a section view taken along the line B-B in FIG. 21B.
Figure 24:
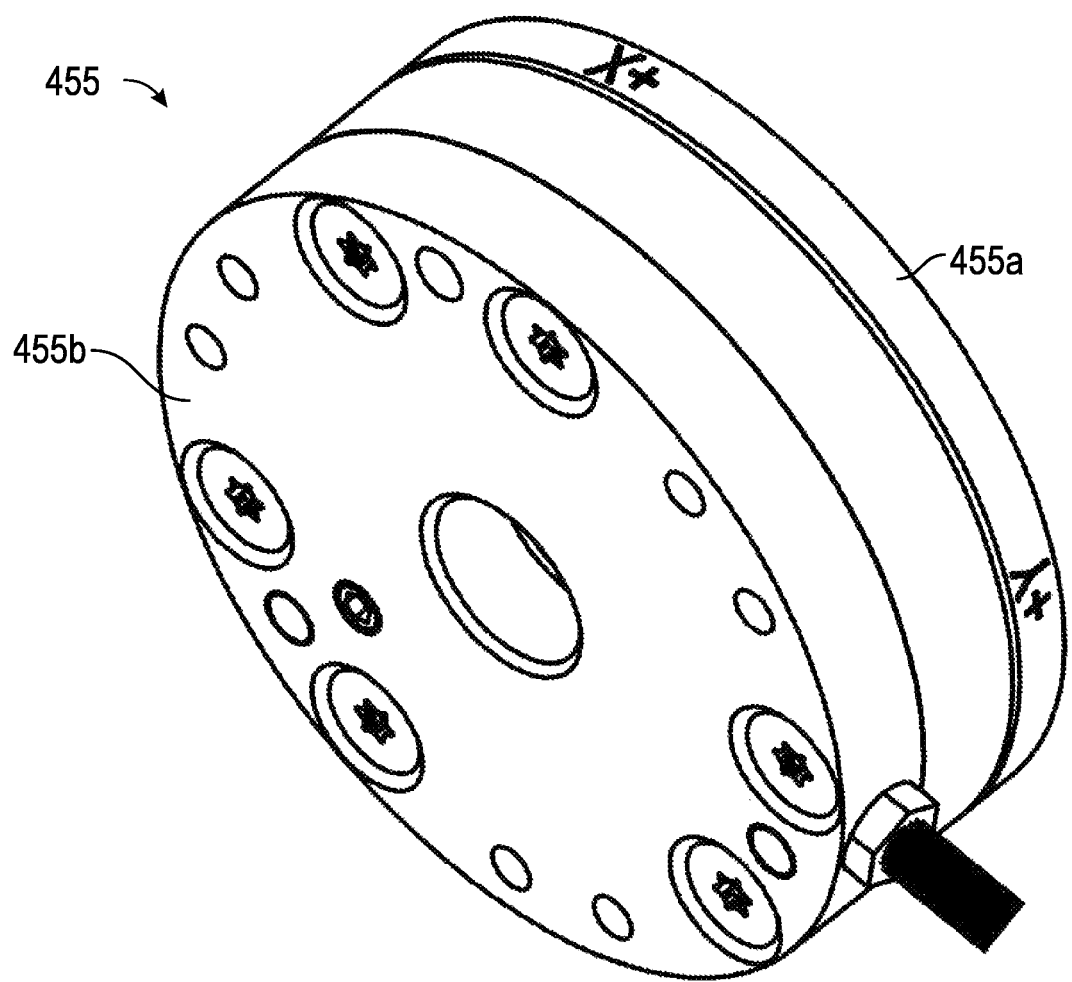
FIG. 24 shows an example of a load cell.

The first and second shell members can be coupled together and include one or more flexures or deflectable elements. Strain measurements of the deflectable elements can be used to calculate forces and moments acting on either of the first and second shell members (e.g., forces in the x, y, and/or z directions and/or moments about the x, y and/or z axes. In a linear regime, the amount of flexure can be directly proportional to the amount of external force or torque applied to the deflectable element. Accordingly, the load cell can measure an entire range of forces and moments on the distal portion of the robotic arm 200. The load cell 255 can sense moments in multiple directions including moments that are applied perpendicular to the plane in which the load cell 255 is mounted (i.e., into/out of the page as shown in FIG. 22A). The load cell can be a multi-axis load cell, a 3-axis load cell (e.g., x, y, z direction forces), or a 6-axis load cell (e.g., x, y, z direction forces and Mx, My, Mz moments). An exemplary embodiment of a load cell 455 (including first plate 455a and second plate 455b, with one or more flexures therebetween) is shown in FIG. 24.

The first end 255a can be located on a proximal side of the structural break 250. The second end 255b can be located on a distal side of the structural break 250. The first end 255a can be coupled with the proximal portion 224a. The second end 255b can be coupled with the distal portion 224b. The first end 255a can be coupled with the proximal portion 224a by one or more mechanical fasteners (not shown). The second end 255b can be coupled with the distal portion 224b by one or more mechanical fasteners 256a-b. The second end 255b can include one or more threaded apertures for receiving the mechanical fasteners 256a-256b. The proximal portion 224a can include a transverse distal wall. The first end 255a can be coupled with the transverse distal wall. The distal portion 224b can include a transverse proximal wall. The second end 255b can be coupled with the transverse proximal wall. The mechanical fasteners 256a-256b can be extendable through apertures in the respective transverse walls and into the respective ends of the load cell 255.

The distal portion of the robotic arm 200 can include the medical instrument 235, the tool driver 230, the fifth link 225 and the distal portion 224b of the fourth link 224. The proximal portion of the robotic arm 200 can include the proximal portion 224a of the fourth link 224, and the links 223, 222, 221 and the support rail 220. The distal portion of the robotic arm 200 can be supported entirely by the load cell 255. The load cell 255 can provide a rigid structural linkage across the structural break 250. Any forces or moments F on the distal end can be detected and/or measured by the load cell 255. The load cell 255 can generate an electrical signal indicating the forces or moments F. Each force or moment (e.g., torque) measured can be output in an electrical signal. Accordingly, a 6-axis load cell can have at least six strain gauges and six outputs. A 3-axis load cell can have three strain gauges and three outputs.

In other implementations, the load cell 255 can be positioned to support the tool driver 230 and the medical instrument 235. The distal portion can comprise the tool driver 230 and the medical instrument 235. In other implementations, the load cell 255 can be positioned within the tool driver 230 to measure forces on the medical instrument 235. In other implementations of the robotic arm 200, the load cell 255 can be positioned on any of the series of linkages or the robotic arm 200, the tool driver 230 or the medical instrument 235. The load cell 255 can be adjacent the wrist joint or elbow of the robotic arm 200.

Figure 22B:
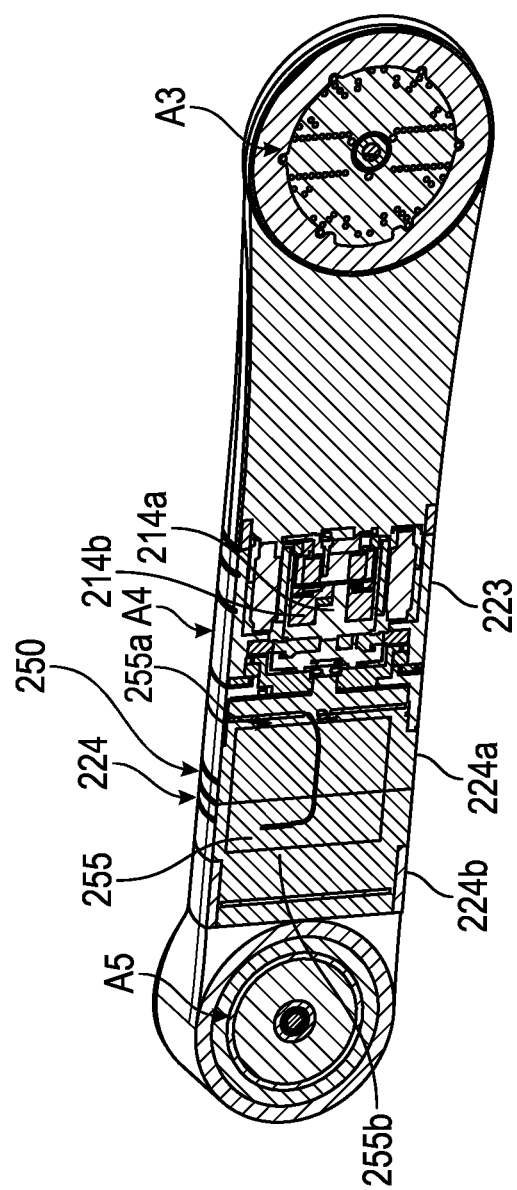
FIG. 22B shows a section view taken along the line A-A in FIG. 21A.

FIG. 22A further shows the fifth joint A5 can include a shaft 215a and a motor 215b. The fifth link 225 can be movable or rotatable about the shaft 215a by action of the motor 215b. The fourth joint A4 can include a shaft 214a and a motor 214b. The shaft 214a can be coupled with the motor 214b. Operation of the motor 214b on the shaft 214a can cause rotation of the fourth link 224 with respect to the third link 223 about the axis of rotation defined by the shaft 214a. FIG. 22B shows another view of the robotic arm 200.

In one implementation, the robotic arm 200 includes more than one load cell (e.g., bridging respective structural breaks). The robotic arm 200 can include a first load cell near the base of the robotic arm (e.g., support rail 220, first link 221, or second link 222) and a second load cell near the tool driver 230 (e.g., third link 223, fourth link 224, fifth link 225, tool driver 230). Two load cells can divide the robotic arm 200 into a proximal portion, intermediate portion, and a distal portion. The inclusion of more than one load cell can provide additional information about forces or moments acting on the robotic arm. For example, the first load cell can measure forces or moments acting on the distal portion and the second load cell can measure forces or moments acting on the distal portion and the intermediate portion.

The load cell 255 incorporated in the robotic arm 200 provide various improvements and advantages to the robotic arm 200. For a medical procedure, one method of operation of the robotic arm 200 is through teleoperation or position control. An operator can position the robotic arm through one or more user inputs (e.g., gimbal 186). Motors or other drivers of each of the articulable joints can be operated to control the positions of the links of the robotic arm 200. This operation mode is primarily position-based. However, the load cell 255 can enable "touch" feedback to the user (e.g., through haptic controls). The load cell 255 can be used to semi-directly measure interaction forces and/or moments between the medical instrument 235 (or other part of the distal portion) and the patient or other objects within the surgical environment (e.g., cannula). If the robotic arm contacts a patient (e.g., body wall), a member of bedside staff, or an object near the bedside can be sensed, the robotic arm 200 can stop to prevent further harm after contacting the object.

Accordingly, the incorporation of the load cell 255 in the robotic arm 200 can be useful for safety during operation of the robotic arm 200. The robotic arm 200 can automatically be limited in the force exerted on an external object. The robotic arm 200 can issue warnings or haptic feedback to the user to limit force exerted. Accordingly, the robotic arm 200 can be prevented from causing further harm to the external object or portions of the robotic arm 200 itself.

In a clinical environment it can also be helpful to have direct manual manipulation of the robotic arm (e.g., back driving). For example, to align the medical instrument 235 with a patient or cannula for insertion therein or to stow or deploy the robotic arm 200 (e.g., from or to a folded/stowed state), the robotic arm 200 can be back driven manually. The load cell 255 can detect interaction forces applied to the distal portion of the robotic arm 200. The robotic arm 200 can be programmed to respond to these forces to allow and/or assist in manipulation of the articulable joints to adjust positions of the robotic arm 200.

In certain implementations, the robotic arm 200 can also include a button (e.g., donut button on the tool driver 230) or other user input for activating an admittance control mode in which interaction forces from a user are detected or measure using the load cell 255. The robotic arm 200 can be controlled to move the robotic arm 200 at least partially in response to the interaction forces in the admittance control mode. For example, a user can select the button and grasp the distal portion of the robotic arm 200 to move the robotic arm in the desired direction. Release of the button can then allow the robotic arm 200 to go back to its operation before activation. In other implementations, the load cell 255 can act as a sensor to activate the admittance control mode.

Figure 23A:
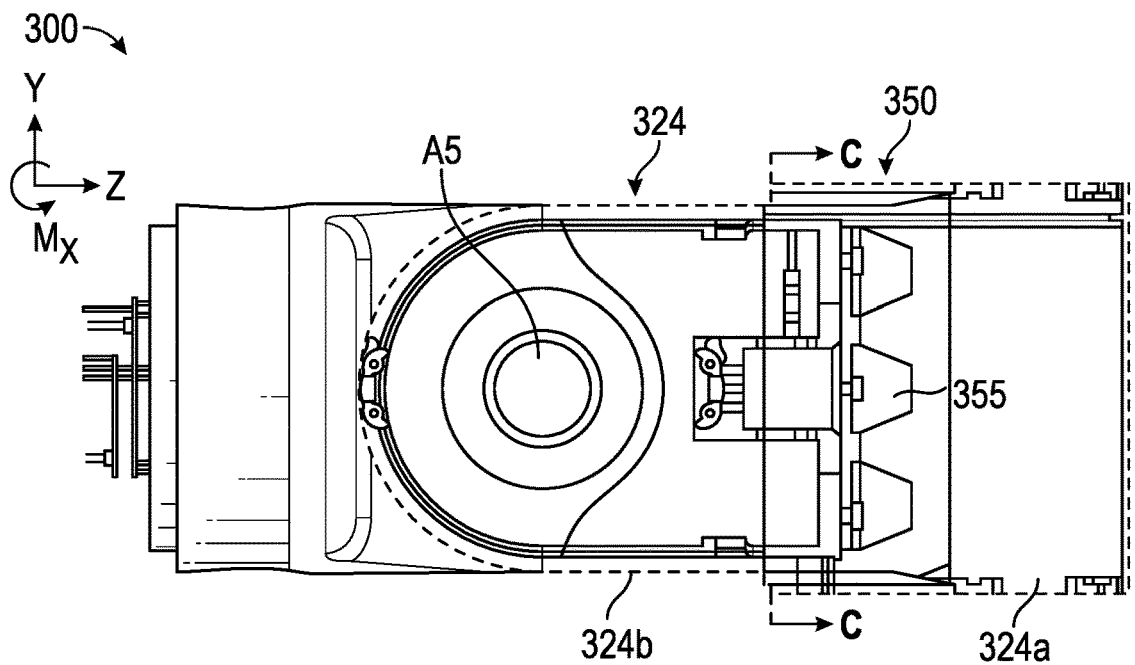
FIG. 23A shows another example of a joint of a robotic arm including one or more force sensors.
Figure 23B:
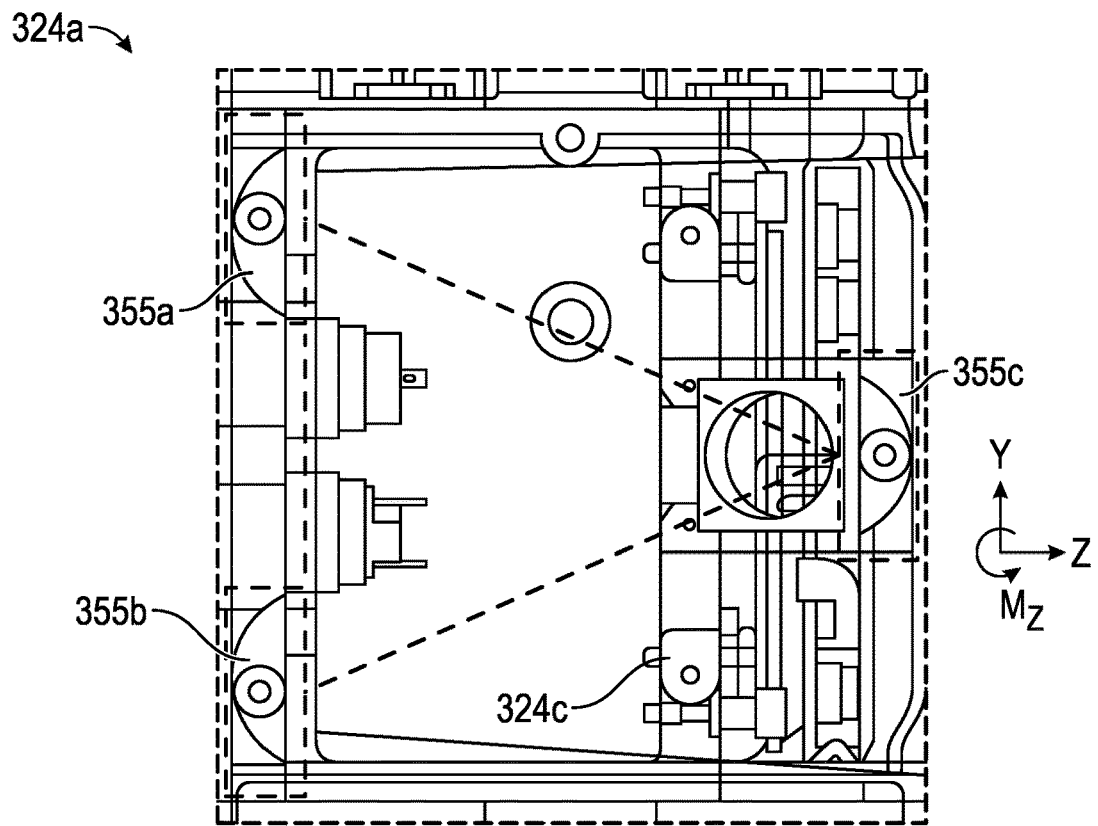
FIG. 23B shows a section view taken along the line C-C in FIG. 23A.

FIGS. 23A and 23B illustrate another embodiment of the robotic arm 300. The robotic arm 300 can include a series of linkages connected by a plurality of articulable joints. The robotic arm 300 can be operated teleoperatively for conducting medical procedures. The robotic arm 300 can include a linkage 324. The linkage 324 can include a proximal portion 324a and a distal portion 324b. The proximal portion 324a can be separated from the distal portion 324b by a structural break 350. The structural break 350 can extend through any structural or exterior portions of the linkage 324. The proximal portion 324a can include a transverse end 324c.

The structural break 350 can advantageously be bridged by a novel load cell 355. The load cell 355 can include three single degree of freedom load cells or force sensors 355a, 355b and 355c. Each of these load cells 355a-355c can include at least one flexure and associated strain gauge. The load cells 355a-355c can operate as a single 3-axis load cell. The load cells 355a-355c can be aligned in a single plane. The single plane can be transverse to a longitudinal axis of the linkage 324.

The load cells 355a-355c can be positioned in a tripod arrangement. The tripod arrangement can form an inherently stable (and not overly constrained) connection between the proximal portion and the distal portion of the arm 300. A first end of each of the load cells 355a-355c and can be fixed with the distal portion 324b. An opposite end of each of the load cells 355a-355c can be coupled with the proximal portion 324a. Accordingly forces (e.g., in x, y, or z directions) or moments (e.g., Mx or My) applied to the distal portion 324b can be measured by the load cells 355a-355c. One exception is that the tripod arrangement of the load cells 355a-c cannot detect moments about the z direction (Mz) due to the load cells 355a-c being in a single plane perpendicular to the moment Mz. In other implementations, the load cell 355 can include individual load cells (e.g., single degree of freedom) in other configurations and other numbers of load cells. In one example, the load cell 355 can be arranged in a square or rectangular pattern and include four load cells.

3. Implementing Systems and Terminology

Implementations disclosed herein provide systems, methods and apparatus for a tool drive supported on a load cell. It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The robotic control functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic surgery system, comprising:
   a robotic arm including a base, a proximal portion and a distal portion;
   a tool driver detachably coupled to a medical instrument, the tool driver coupled with the distal portion of the robotic arm; and
   a load cell positioned between the proximal portion and the distal portion such that the load cell supports the distal portion and the tool driver,
   wherein the load cell is positioned adjacent a wrist joint of the robotic arm, between a first joint and a second joint of the robotic arm, or adjacent the base of the robotic arm,
   wherein the load cell is configured to detect forces that interact with the distal portion or the tool driver.

2. The system of claim 1, further comprising a structural break between the proximal portion and the distal portion, the load cell bridging the structural break.

3. The system of claim 1, wherein the load cell is positioned adjacent the wrist joint of the robotic arm.

4. The system of claim 1, wherein the load cell is positioned between the first joint and the second joint of the robotic arm.

5. The system of claim 4, wherein the first joint is a wrist roll joint and the second joint is a wrist pitch joint.

6. The system of claim 1, wherein the load cell is positioned adjacent the base of the robotic arm.

7. The system of claim 1, wherein the load cell is a multi-axis load cell.

8. The system of claim 1, wherein the load cell comprises a plurality of load cells.

9. The system of claim 8, wherein the plurality of load cells includes at least three load cells.

10. The system of claim 9, wherein the three load cells are arranged in a tripod configuration.

11. The system of claim 8, wherein the load cells of the plurality of load cells are single-axis load cells.

12. The system of claim 1, wherein the load cell is a first load cell and further comprising a second load cell positioned between the base and the first load cell, the second load cell supporting the first load cell and the distal portion including the tool driver, the second load cell configured to detect forces that interact with any portion of the robotic arm or tool driver distal to the second load cell.

13. The system of claim 1, wherein the load cell is configured to detect interaction forces between a patient and/or cannula and the tool driver or medical instrument.

14. A robotic surgery system, comprising:
    a robotic arm including a base, a proximal portion and a distal portion;
    a tool driver detachably coupled to a medical instrument, the tool driver coupled with the distal portion of the robotic arm; and
    a multi-axis load cell positioned between the proximal portion and the distal portion;
    wherein the load cell forms a structural break between the proximal portion and the distal portion such that the load cell entirely supports the distal portion including the tool driver.

15. The system of claim 14, wherein the load cell is positioned between a first joint and a second joint of the robotic arm.

16. The system of claim 14, wherein the load cell is positioned adjacent the base of the robotic arm.

17. The system of claim 14, wherein the load cell is configured to detect interaction forces between a patient and/or cannula and the tool driver or medical instrument.

18. A robotic surgery system, comprising:
    a robotic arm including a base, a proximal portion, a distal portion, and a structural break between the proximal portion and the distal portion;

a tool driver detachably coupled to a medical instrument, the tool driver coupled with the distal portion of the robotic arm; and a load cell positioned between the proximal portion and the distal portion such that the load cell supports the distal portion and the tool driver, the load cell bridging the structural break, wherein the load cell is configured to detect forces that interact with the distal portion or the tool driver.

19. A robotic surgery system, comprising:

a robotic arm including a base, a proximal portion and a distal portion;

a tool driver detachably coupled to a medical instrument, the tool driver coupled with the distal portion of the robotic arm; and a load cell positioned between the proximal portion and the distal portion such that the load cell entirely supports the distal portion of the robotic arm and the tool driver, wherein the load cell is configured to detect forces that interact with the distal portion or the tool driver.

20. A robotic surgery system, comprising:

a robotic arm including a base, a proximal portion and a distal portion;

a tool driver detachably coupled to a medical instrument, the tool driver coupled with the distal portion of the robotic arm; and a load cell positioned between the proximal portion and the distal portion such that the load cell supports the distal portion and the tool driver, the load cell comprising a first shell member and a second shell member, the first shell member coupled with the distal portion of the robotic arm and the second shell member coupled with proximal portion of the robotic arm, wherein the load cell is configured to detect forces that interact with the distal portion or the tool driver.

* * * * *